(12) United States Patent
Fujii et al.

(10) Patent No.: US 9,566,615 B2
(45) Date of Patent: Feb. 14, 2017

(54) RESIN PIECE SORTING METHOD AND RESIN PIECE SORTING APPARATUS

(71) Applicant: Mitsubishi Electric Corporation, Chiyoda-ku (JP)

(72) Inventors: Noriyuki Fujii, Chiyoda-ku (JP); Jiro Naka, Chiyoda-ku (JP)

(73) Assignee: Mitsubishi Electric Corporation, Chiyoda-ku (JP)

( * ) Notice: Subject to any disclaimer, the term of this patent is extended or adjusted under 35 U.S.C. 154(b) by 0 days.

(21) Appl. No.: 14/826,536

(22) Filed: Aug. 14, 2015

(65) Prior Publication Data

US 2016/0074910 A1 Mar. 17, 2016

(30) Foreign Application Priority Data

Sep. 17, 2014 (JP) ................................. 2014-188592
May 18, 2015 (JP) ................................. 2015-100916

(51) Int. Cl.
  *B07C 5/34* (2006.01)
  *B07C 5/346* (2006.01)
  *G01N 23/087* (2006.01)

(52) U.S. Cl.
  CPC ............ *B07C 5/346* (2013.01); *B07C 5/3416* (2013.01); *G01N 23/087* (2013.01)

(58) Field of Classification Search
  CPC .... B07C 5/3416; B07C 5/3425; B07C 5/3427; G01N 23/083; G01N 23/087
  See application file for complete search history.

(56) References Cited

U.S. PATENT DOCUMENTS

| | | | | |
|---|---|---|---|---|
| 5,164,590 | A * | 11/1992 | Coles ................... | G01N 23/046 250/253 |
| 6,377,652 | B1 * | 4/2002 | Sturm .................... | G01N 23/06 378/157 |
| 7,763,820 | B1 * | 7/2010 | Sommer, Jr. ............ | B07C 5/346 209/576 |

(Continued)

FOREIGN PATENT DOCUMENTS

| | | | | |
|---|---|---|---|---|
| JP | | 8-81038 A | 3/1996 | |
| JP | DE 102009013389 A1 * | | 10/2009 | ............. B07C 5/344 |

(Continued)

*Primary Examiner* — Joseph C Rodriguez
(74) *Attorney, Agent, or Firm* — Oblon, McClelland, Maier & Neustadt, L.L.P.

(57) ABSTRACT

The sorting method includes: an X-ray inspection step of irradiating a resin piece with X-rays including a first X-ray and a second X-ray having respective energy ranges different from each other and measuring a first transmission intensity which is an intensity of the first X-ray transmitted through the resin piece and a second transmission intensity which is an intensity of the second X-ray transmitted through the resin piece; a first determination step of making a determination as to whether the resin piece is a candidate for a useful resin piece, using the first transmission intensity; and a second determination step of making a determination as to whether a resin piece identified as a candidate for a useful resin piece in the first determination step is a useful resin piece, using a differential value obtained from the first transmission intensity and the second transmission intensity.

9 Claims, 12 Drawing Sheets

(56) References Cited

U.S. PATENT DOCUMENTS

| | | | | |
|---|---|---|---|---|
| 8,742,277 | B2* | 6/2014 | Tavakkoli | B07C 5/3425 209/589 |
| 8,855,809 | B2* | 10/2014 | Spencer | B07C 5/3416 378/53 |
| 2001/0045518 | A1* | 11/2001 | Sommer, Jr. | B07C 5/3416 250/339.06 |
| 2004/0066890 | A1* | 4/2004 | Dalmijn | G01N 23/12 378/57 |
| 2009/0261024 | A1* | 10/2009 | Sommer, Jr. | G01N 23/06 209/589 |
| 2010/0219109 | A1* | 9/2010 | Roos | B07C 5/3416 209/3.1 |
| 2013/0304254 | A1* | 11/2013 | Torek | B07C 5/3416 700/223 |
| 2016/0038979 | A1* | 2/2016 | Kazakov | B07C 5/346 209/589 |

FOREIGN PATENT DOCUMENTS

| | | |
|---|---|---|
| JP | 2009-279541 A | 12/2009 |
| JP | 2010-091483 | 4/2010 |
| WO | WO 2008/126892 A1 | 10/2008 |

* cited by examiner

RESIN PIECE SORTING METHOD AND RESIN PIECE SORTING APPARATUS

BACKGROUND OF THE INVENTION

Field of the Invention

The present invention relates to a resin piece sorting method and a resin piece sorting apparatus, and particularly relates to a method of sorting resin pieces for removing the resin pieces containing a specific element, from a large number of resin pieces including various kinds of resins and from foreign materials other than the resin, which have irregular shapes, as well as a resin piece sorting apparatus for which this method is used.

Description of the Background Art

When an object made of a certain substance is irradiated with X-rays, the amount of X-rays absorbed by the object is determined by the kinds and density of elements contained in the object as well as the thickness of the object. In order to differentiate between a plurality of objects made of different materials based on X-ray absorption characteristics, it is necessary to take into consideration the influence of an element contained in an object on X-ray absorption and the influence of the thickness of an object on X-ray absorption. In the case where the former influence is larger than the latter influence, what material makes an object can be determined based on the X-ray transmittance. For example, when a metal foreign material contained in a food is to be identified, whether or not the metal foreign material is contained can be determined merely by acquiring an X-ray transmission image.

In the case however where respective atomic numbers of elements contained respectively in samples are close to each other, the influence of the thickness of an object on X-ray absorption is not negligible, relative to the influence of a contained element on X-ray absorption. It is therefore fundamentally difficult to differentiate, based on the amount of absorbed X-rays, between substances contained respectively in a large number of objects having respective shapes different from each other.

In the case where an object contains substances having respective X-ray absorption tendencies close to each other, identification for example of a bone in a body tissue or a bone foreign material in a food by measuring absorption of X-rays can be done by means of a technique known as energy subtraction method. According to the energy subtraction method, two kinds of X-rays having respective energy regions different from each other are applied to an object, respective characteristics of absorption of these X-rays are measured, and the difference therebetween is calculated to thereby enable highly sensitive detection of a difference between substances contained in the object. Specifically, for an object to be measured, a characteristic of its absorption of a low energy X-ray and a characteristic of its absorption of a high energy X-ray are measured, a natural logarithm of the transmittance of each X-ray is taken, a weight is applied by an appropriately selected parameter, and thereafter the difference is calculated. As will be described later herein, a weighting factor can appropriately be selected so that the differential value for a specific substance in the object is theoretically zero, regardless of the thickness of the object. Accordingly, the specific substance can be discriminated from other substances with high sensitivity.

In order to use the energy subtraction method, it is necessary to measure absorption of two kinds of X-rays having respective energies different from each other. Formerly two X-ray sources and two X-ray sensors were used. Currently an X-ray source generating continuous X-rays and a dual energy X-ray sensor capable of detecting each of absorption of a low energy X-ray and absorption of a high energy X-ray are used. One X-ray source and one dual energy X-ray sensor are used to enable the energy subtraction method to be utilized.

In order to make the most of the effects of the energy subtraction method, it is necessary to set the weighting parameter to an optimum weighting parameter. As a technique for automatically setting the parameter, a technique has been proposed that acquires an image with the intensity of transmitted X-rays and thereafter makes an independent component analysis (see Japanese Patent Laying-Open No. 2010-91483 for example). According to this technique, an image in which only a substance to be identified is enhanced can be obtained through a series of: acquisition of an image; image conversion for the independent component analysis; setting of a parameter from the converted image; and acquisition of an image in which only a foreign material is enhanced.

Meanwhile, the waste plastic recycling business requires a technique of accurately differentiating resin pieces and metal foreign materials to be removed that contain additives which hinder recycling, from resin pieces of miscellaneous waste plastics, and sorting only useful resin pieces appropriate for recycling.

SUMMARY OF THE INVENTION

In the case where the technique of the above-described energy subtraction method is applied to a recycle plant for resin materials obtained from waste household electrical products so as to differentiate and sort a useful resin material from resin materials containing additives inappropriate for recycling, it is necessary to take into account the following issues.

1. Resin pieces to be sorted are a mixture of resin pieces resultant from shredding of resin parts containing a variety of additive materials. There are a wide variety of additive materials to be removed by sorting.

2. Many resin pieces irregularly placed on a conveyor apparatus are individually identified, and therefore, multiple operations have to be done simultaneously and speedily.

The additives hindering resin materials from being recycled are glass fiber and bromine-based flame retardant, for example. In the industrial respect, a resin containing these additive materials having different properties has to be identified and removed by means of one apparatus.

Moreover, in order to simultaneously and speedily sort a plurality of resin pieces, it is not appropriate to use an advanced process such as image diagnosis. It is thus necessary to sort a resin piece by directly using, for each measurement of the resin piece to be sorted, the differential value calculated based on the energy subtraction method. The inventors of the present application have found that in the case where there are multiple kinds of additive materials to be removed and elements constituting respective additive materials are different from each other in terms of the absorption tendency for X-rays, accurate discrimination based on a determination by a comparison with a preset threshold value may be impossible in some cases.

Particularly in the case where the energy subtraction method is applied to sorting in a resin-material recycle plant, the influence of the aforementioned issues is considered as more significant, since foreign materials to be measured may include the metal in some cases.

The present invention has been made to solve the problems as described above, and an object of the present invention is to provide a sorting method for sorting recyclable resin pieces by speedily differentiating the recyclable resin pieces from resin materials inappropriate for recycling and foreign materials other than the resin, among a mixture of resin pieces containing a wide variety of materials, as well as a sorting apparatus for which this method is used to sort resin pieces.

It should be noted that sorting herein refers to an act of picking up a material (reusable material) recognized as useful for the reason for example that it is recyclable.

A resin piece sorting method of the present invention includes: an X-ray inspection step of irradiating a resin piece with X-rays including a first X-ray and a second X-ray having respective energy ranges different from each other and measuring a first transmission intensity which is an intensity of the first X-ray transmitted through the resin piece and a second transmission intensity which is an intensity of the second X-ray transmitted through the resin piece; a first determination step of making a determination as to whether the resin piece is a candidate for a useful resin piece, using the first transmission intensity; a second determination step of making a determination as to whether a resin piece identified as a candidate for a useful resin piece in the first determination step is a useful resin piece, using a differential value obtained from the first transmission intensity and the second transmission intensity; and a collection step of collecting a resin piece identified as useful based on a result of the determination in the second determination step.

A resin piece sorting apparatus of the present invention includes: a conveying unit conveying a resin piece; an X-ray irradiation unit irradiating the resin piece with X-rays including a first X-ray and a second X-ray having respective energy ranges different from each other; an intensity-of-transmitted-X-ray measurement unit measuring a first transmission intensity which is an intensity of the first X-ray transmitted through the resin piece and a second transmission intensity which is an intensity of the second X-ray transmitted through the resin piece; a first determination unit making a determination as to whether the resin piece is a candidate for a useful resin piece, using the first transmission intensity; a second determination unit making a determination as to whether a resin piece identified as a candidate for a useful resin piece by the first determination unit is a useful resin piece, using a differential value obtained from the first transmission intensity and the second transmission intensity; and a sorting unit sorting and collecting the resin piece, based on a result of the determination by the second determination unit.

According to the resin piece sorting method of the present invention, the intensity of the transmitted X-ray is measured, the determination is made in the first determination step in the first stage, and thereafter the determination is made in the second determination step in the second stage using the energy subtraction method. In this way, resin pieces to be reclaimed and resin pieces to be removed or foreign materials such as metal to be removed can be speedily discriminated from each other. Further, in the case where resin pieces contain multiple kinds of elements, the resin pieces can be sorted as well by the determination made with high accuracy.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiments of the invention will hereinafter be described with reference to the drawings. It should be noted that the present invention is particularly effective for use with the case where an object to be sorted is a resin piece and the resin piece to be used for recycling is sorted from waste plastics. In the following, therefore, a description will be given of an example where a resin piece of a waste plastic is used as an object to be sorted.

First Embodiment

Many plastic raw materials used for household electrical products and the like contain glass fibers for increasing the strength, or a flame retardant which is added for making the product flame-resistant. In order to reclaim waste plastics from waste household electrical products and the like and use the plastics again as plastic raw materials, it is necessary to remove resin pieces made of plastics containing the aforementioned additives and sort only the resin pieces made of useful plastic materials. Here, a resin piece which does not contain additives or the like that hinder recycling and is desired to be sorted for use with recycling is referred to as "useful resin piece." It should be noted that "additive" herein refers to an additive containing elements other than elements with small atomic numbers (that are herein hydrogen (H), carbon (C), nitrogen (N), oxygen (O)) which are main components of a resin. A resin piece containing a slight amount of the additive can be used for recycling and may be treated as a useful resin piece.

In the case where a resin piece contains glass fibers, the resin piece contains an element like silicon (Si) with a low absorptance of a relatively high energy X-ray, as compared with its absorptance of a relatively low energy X-ray. In the following, such a resin piece is referred to as a foreign material of small X-ray absorption.

The flame retardant contains an element like bromine (Br) as an additive, and therefore, its absorptance of a relatively high energy X-ray is not lower relative to its absorptance of a relatively low energy X-ray. Further, a foreign material made of a metal itself obviously exhibits large X-ray absorption. In the following, a resin piece and a metal piece to which bromine is added are collectively referred to as foreign materials of large X-ray absorption. The foreign material of small X-ray absorption and the foreign material of large X-ray absorption are herein collectively referred to as objects to be removed.

Figure 1:
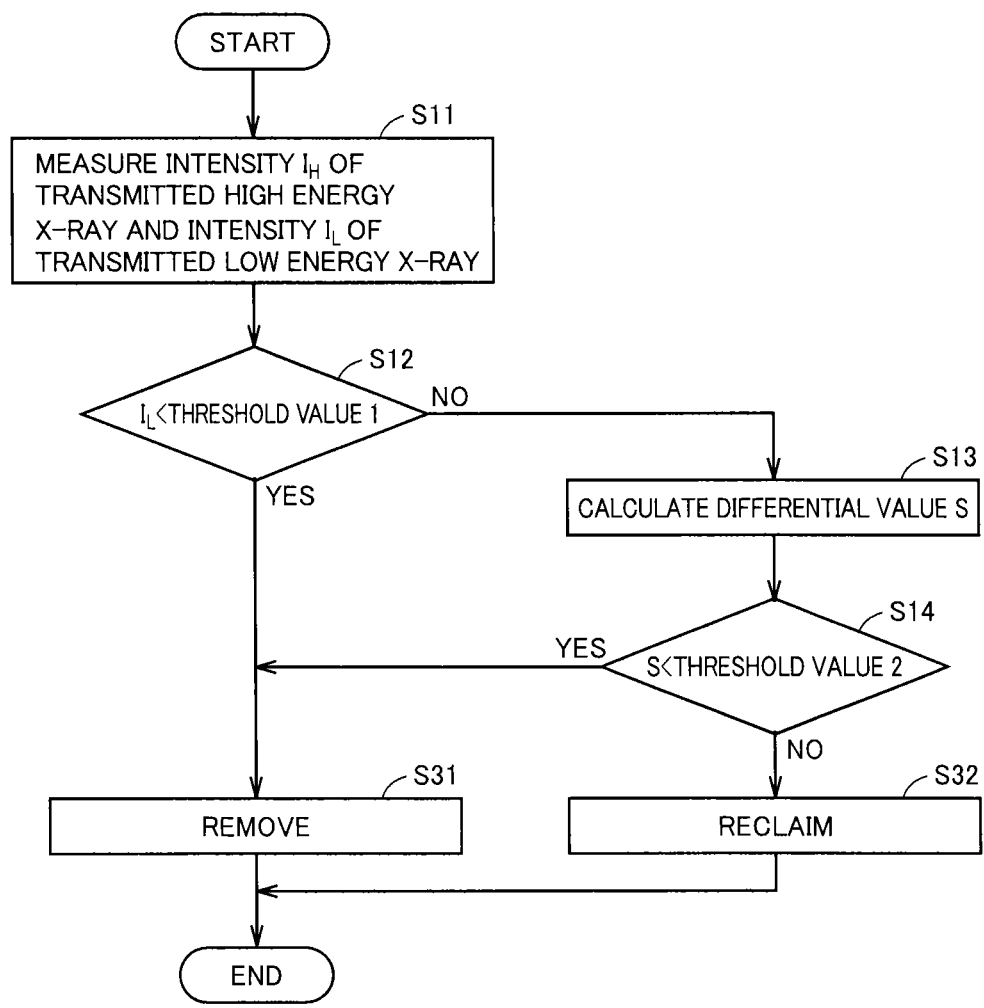
FIG. 1 is a determination flowchart for making a determination to distinguish between useful resin pieces and objects to be removed, in a first embodiment of the present invention.

FIG. 1 is a diagram showing a determination flowchart for making a determination to distinguish between useful resin pieces and objects to be removed, in a first embodiment for implementing the present invention.

First, in step S11, an X-ray irradiation unit irradiates an object to be measured with a low energy X-ray and a high energy X-ray having respective energy ranges different from each other, and respective intensities $I_H$, $I_L$ of the transmitted X-rays are acquired by an X-ray sensor. Namely, step S11 is an X-ray inspection step. The low energy X-ray and the high energy X-ray used here may have respective wavelength regions different from each other in the continuous X-ray spectrum. Ideally it is desired that respective intensities of the transmitted X-rays are measured at the same point and at the same timing. This manner of measurement can be done by the X-ray irradiation unit irradiating an object with X-rays using an X-ray source which generates continuous X-rays and by the X-ray sensor capable of simultaneously measuring intensity $I_L$ of the transmitted low energy X-ray and intensity $I_H$ of the transmitted high energy X-ray. Such an X-ray sensor may be the one having a structure made up of a combination of two different types of scintillator-mounted photodiode arrays arranged at an upper stage and a lower stage respectively. The upper array detects a low energy X-ray and the lower array detects a high energy X-ray transmitted through the upper array.

Next, in step S12, a control device such as sequencer compares intensity $I_L$ of the transmitted low energy X-ray with preset Threshold Value 1 (first determination step). Here, as a method of setting Threshold Value 1, a method is used according to which the intensities of transmitted X-rays are measured in advance for a group of useful resin pieces having the maximum thickness that the known useful resin pieces can have, and Threshold Value 1 is set to a value lower than the intensities of transmitted X-rays for all the useful resin pieces. In the case where Threshold Value 1 which is set in this manner is used, the intensities of transmitted X-rays for all the useful resin pieces are higher than Threshold Value 1.

When the comparison by the control device between intensity $I_L$ of the transmitted X-ray and Threshold Value 1 results in the fact that intensity $I_L$ of the transmitted X-ray is smaller than Threshold Value 1 (YES in S12), the process proceeds to step S31.

In step S31, the control device determines that the object to be measured is an object to be removed.

When intensity $I_L$ of the transmitted X-ray is equal to or more than Threshold Value 1 (NO in S12), the control device determines that the object to be measured is a candidate for a useful resin piece. A resin piece containing no additive is made of elements with small atomic numbers. Therefore, when such a resin piece and a resin piece containing other elements in its additive that are of the same thickness are compared with each other, the latter resin piece absorbs more X-rays than the former resin piece.

Figure 2:
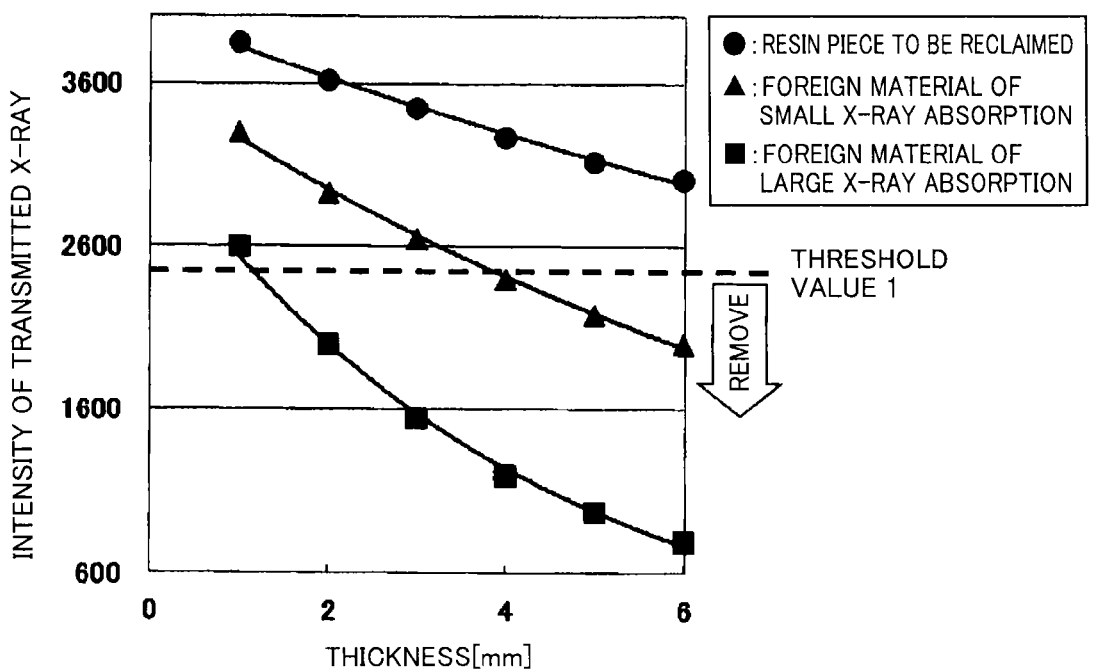
FIG. 2 is a diagram showing a relation between the intensity of a transmitted low energy X-ray and the thickness of a resin piece, in the first embodiment of the present invention.

FIG. 2 is a diagram showing a relation between the intensity of a transmitted low energy X-ray and the thickness of a resin piece, and illustrating how the determination is made with respect to Threshold Value 1. In FIG. 2, the results of an experiment conducted for principle verification are shown. The horizontal axis in FIG. 2 represents the thickness of a resin piece which is an object to be measured, and the vertical axis in FIG. 2 represents the intensity of a transmitted low energy X-ray. Here, the intensity of a transmitted X-ray (intensity of incidence) when there is no object to be measured is set to 4095. The points represented by circles are the results obtained from useful resin pieces, the points represented by triangles are the results obtained from foreign materials of small X-ray absorption, and the points represented by rectangles are the results obtained from foreign materials of large X-ray absorption. For each of the different types of objects to be measured, the points correspond to thicknesses with an increment of 1 mm, and the results obtained from the objects to be measured of the same type are connected by a solid line.

Regarding the measurement in FIG. 2, the useful resin piece contains no additive. As the foreign material of small X-ray absorption, a resin containing glass fibers (containing the element Si) as an additive was used. As the foreign material of large X-ray absorption, a resin containing 5 wt % of a bromine-based flame retardant (containing the element Br) was used. As the X-ray source, an X-ray tube with a tungsten target was used and X-rays were generated at a tube voltage of 50 kV. The tungsten target can generate continuous X-rays of high intensity and it is an X-ray source appropriate for the use of the present application. Beside this, a target such as rhodium (Rh), molybdenum (Mo), chromium (Cr) or the like that generates not only continuous X-rays but also a characteristic X-ray at a tube voltage of 50 kV or less can be used on the condition that the absorption band of the object to be measured is taken into consideration.

In FIG. 2, the broken line in the direction of the horizontal axis represents Threshold Value 1 set in advance. The control device determines that an object to be measured with an intensity of the transmitted X-ray smaller than Threshold Value 1 is an object to be removed, and determines that an object to be measured with an intensity of the transmitted X-ray equal to or larger than Threshold Value is a candidate for an object to be sorted. It should be noted that the control device may determine that an object to be measured with an intensity of the transmitted X-ray equal to Threshold Value 1 is an objet to be removed.

In the case of resin pieces made of waste plastics, the resin pieces are not uniform in size and the plastics forming the resin pieces are of several kinds. Therefore, the actual values of the intensity of the transmitted X-ray vary depending on various factors. Accordingly, while the ratio of reclaimed useful resin pieces will increase if Threshold Value 1 is set smaller, the reclaimed resin pieces will include objects to be removed that have a high intensity of the transmitted X-ray and a small thickness. In contrast, while the ratio of reclaimed useful resin pieces will decrease if Threshold Value 1 is set larger, many objects can be removed.

Namely, as is apparent from FIG. 2, there remain objects to be removed that cannot be removed through the determination based on only the intensity of the transmitted X-ray. This is for the reason that absorption of the X-ray is influenced not only by the elements contained in the object to be measured but also by the thickness of the object to be measured. When it is determined in step S12 that the object to be measured is not an object to be removed, the process proceeds to the step of calculating a differential value in step S13.

In step S13, the control device calculates a differential value S based on the energy subtraction method, from intensity $I_L$ of the transmitted low energy X-ray and intensity $I_H$ of the transmitted high energy X-ray that are obtained in step S11. Here, how to calculate the differential value will be specifically described.

The relations represented by the following formulas (1) and (2) hold, where $I_L$ is the intensity of the transmitted low energy X-ray regarding an object to be measured, $I_H$ is the intensity of the transmitted high energy X-ray regarding the object to be measured, $\mu_L$ is an attenuation coefficient for the low energy X-ray, $\mu_H$ is an attenuation coefficient for the high energy X-ray, $I_0$ is the intensity of the X-ray radiation, and t is the thickness of the object to be measured. In FIG. 2, the horizontal axis represents t of formula (1) and the vertical axis represents $I_L$ thereof.

$$I_L = I_0 e^{(-\mu_L t)} \quad (1)$$

$$I_H = I_0 e^{(-\mu_H t)} \quad (2)$$

Natural logarithms of both sides of the formulas (1) and (2) are taken, which are represented by the following formulas (3) and (4), respectively.

$$\log_e(I_L/I_0) = -\mu_L t \quad (3)$$

$$\log_e(I_H/I_0) = -\mu_H t \quad (4)$$

Subtraction is done between respective values of the solutions to formulas (3) and (4) multiplied by a differential value parameter which is an arbitrary constant, and the value of the difference therebetween is referred to as a differential value. The differential value is determined based on the following formula (5) where k is the differential value parameter and S is the differential value.

$$S = \log_e(I_L/I_0) - k \cdot \log_e(I_H/I_0) = -(\mu_L - k \cdot \mu_H) t \quad (5)$$

In order to actually calculate differential value S, it is necessary to set differential value parameter k in advance. As seen from formula (5), differential value S is the product of thickness t and the term $(\mu_L - k \cdot \mu_H)$ calculated from the attenuation coefficients depending on the density and the material which is the contained element of the object to be measured, and is basically a value influenced by thickness t, like the intensity of the transmitted X-ray. However, when k is set to a value that causes $(\mu_L - k \cdot \mu_H)$ to be zero, S=0 can accordingly be obtained regardless of thickness t of the object to be measured. For useful resin pieces, k can be set so that S=0 holds, to thereby make it theoretically possible to determine that an object for which S is any value other than zero is an object to be removed. An example of the method of setting differential value parameter k may be as follows. For known useful resin pieces, multiple intensities of the transmitted low energy X-ray and multiple intensities of the transmitted high energy X-ray are measured in advance, and k may be set to a value that allows an average of differential values S to be closest to 0.

Differential value S calculated in this manner is compared with Threshold Value 2 for the differential value by the second determination (second determination step) in step S14. Threshold value 2 may be set in the following way. Similarly to setting of Threshold Value 1, for known useful resin pieces, differential value parameter k is set in advance as described above, parameter k is used to calculate differential value S, and Threshold Value 2 is set to a value smaller than differential values S of all the useful resin pieces.

Figure 3:
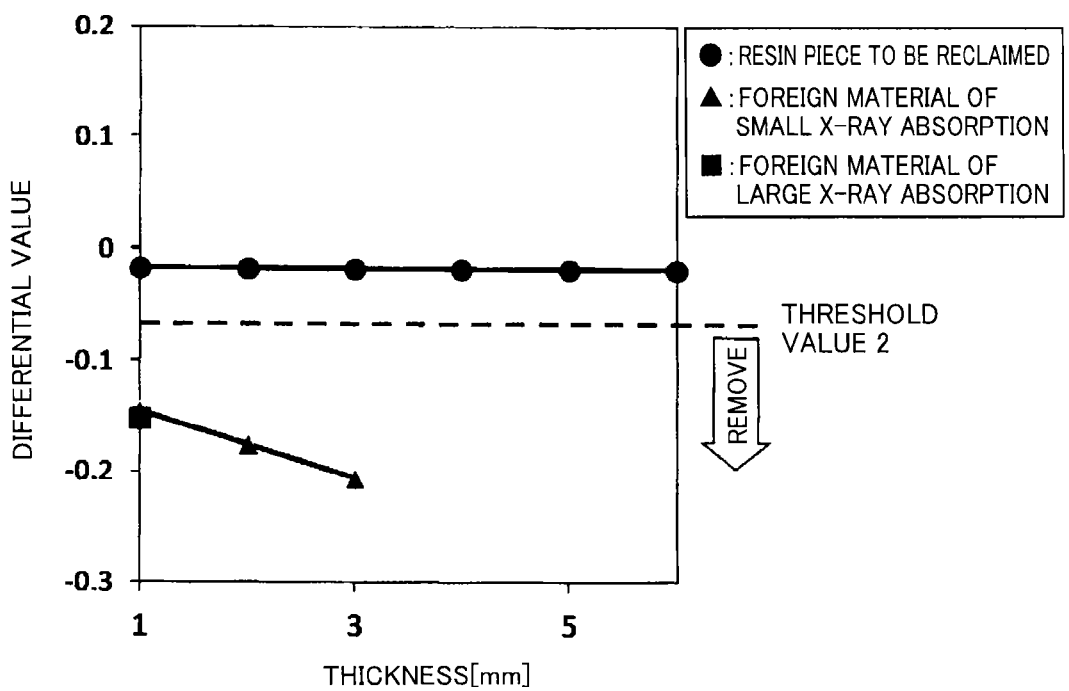
FIG. 3 is a diagram showing a relation between a differential value and the thickness of an object to be measured, after a first determination step, for illustrating a determination method according to the first embodiment of the present invention.

FIG. 3 is a diagram showing a relation between the differential value and the thickness of the object to be measured after the first determination step, and illustrates a situation when differential value S of the object to be measured is compared with Threshold Value 2 in step S14. In FIG. 3, the horizontal axis represents the thickness of the object to be measured, and the vertical axis represents differential value S. Like FIG. 2, the points represented by circles are the results obtained from useful resin pieces, the points represented by triangles are the results obtained from foreign materials of small X-ray absorption, and the point represented by a rectangle is the result obtained from foreign materials of large X-ray absorption. The points for foreign materials of small X-ray absorption and foreign materials of large X-ray absorption that have large thicknesses are not shown in FIG. 3 since the determination for them is done already in step S12. As seen from the points for the useful resin pieces, when the differential value parameter which is set in the above-described way is used, differential value S for the useful resin piece does not depend on the thickness of the useful resin piece and is rather a value around zero. Threshold Value 2 can therefore be set as indicated by the broken line in FIG. 3 to distinguish, with high sensitivity, between useful resin pieces and objects to be removed.

In step S14, when the control device compares differential value S regarding the object to be measured with Threshold Value 2 and differential value S regarding the object to be measured is smaller than Threshold Value 2 (YES in S14), the process proceeds to step S31. When differential value S regarding the object to be measured is equal to or more than Threshold Value 2 (NO in S14), the process proceeds to step S32.

In step S31, the control device determines that the object to be measured is an object to be removed.

In step S32, the control device determines that the object to be measured is a useful resin piece. Whether an object for which the differential value is equal to Threshold Value 2 is to be categorized as an object to be removed or a useful resin piece may be determined as appropriate.

After the determination about whether the object is a useful resin or not is made, the useful resin is collected and reclaimed (collection step). The object to be removed is differentiated from useful resins and removed.

Here, a detailed description will be given about the reason why it is necessary to perform sorting through the determinations in the two stages like the first embodiment, rather than only the differential value is used for making the determination to distinguish foreign materials.

It has been considered possible to distinguish between useful resin pieces and objects to be removed, through the determination in steps S13 to S14, namely the determination based on the differential value only. The inventors of the present application, however, have noted that in the case where objects to be removed contain a variety of elements, like the case where objects to be measured are waste plastics to be recycled, the determination based on only the differential value may result in an erroneous determination.

Figure 4:
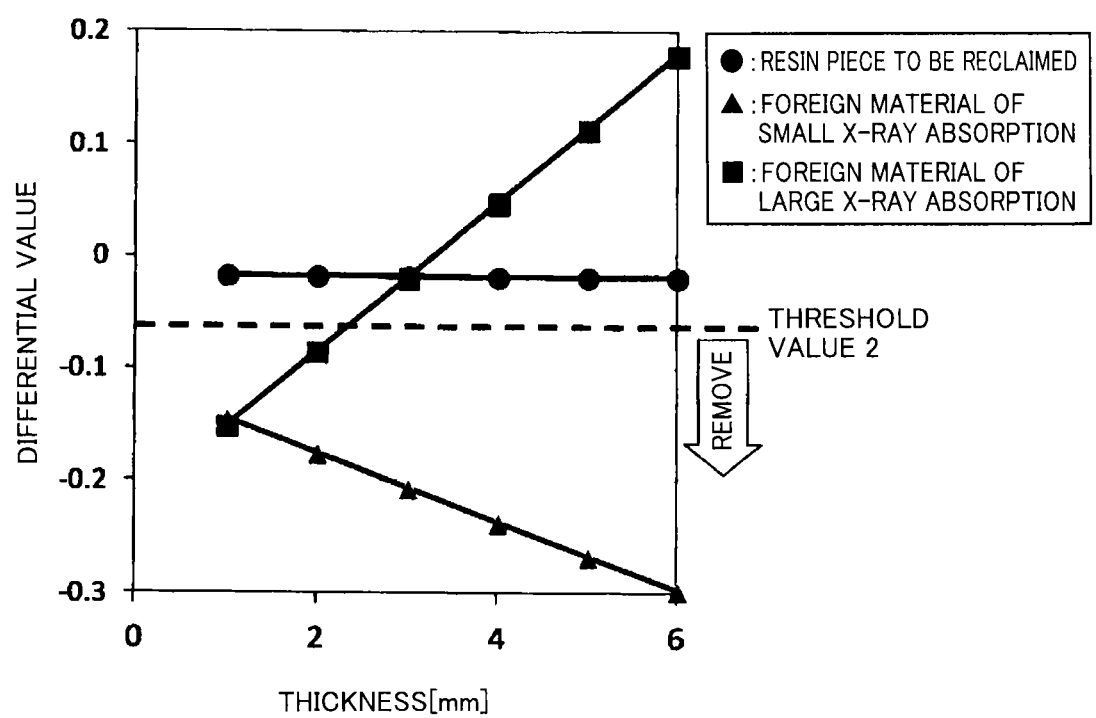
FIG. 4 is a diagram showing a relation between differential value S and the thickness of an object to be measured, for illustrating the determination method according to the first embodiment of the present invention.

FIG. 4 is a diagram showing a relation between differential value S and the thickness of the object to be measured, for illustrating the determination method in the first embodiment. In FIG. 4, the horizontal axis represents the thickness of the object to be measured and the vertical axis represents differential value S calculated from intensity $I_L$ of the transmitted low energy X-ray and intensity $I_H$ of the transmitted high energy X-ray regarding the object to be measured. The points represented by circles indicate data about useful resin pieces, the points represented by triangles indicate data about foreign materials of small X-ray absorption, the points represented by rectangles indicate data about foreign materials of large X-ray absorption, and the position of Threshold Value 2 is represented by a broken line.

As seen from FIG. 4, the foreign material of small X-ray absorption and the foreign material of large X-ray absorption differ from each other in terms of a response of the differential value to the thickness. Therefore, if it is determined that objects to be measured whose differential value is Threshold Value 2 or less are objects to be removed, an erroneous determination will be made particularly for foreign materials of large X-ray absorption. Here, what causes this erroneous determination will be described.

According to formula (5), differential value S is the product of the term $-(\mu_L - k \cdot \mu_H)$ and t. Thus, the difference in the response to thickness t as shown in FIG. 4 is generated due to the difference in terms of whether $-(\mu_L - k \cdot \mu_H)$ is positive or negative. As to the terms in $-(\mu_L - k \cdot \mu_H)$, the value of k is a value for setting a useful resin piece as a reference. The values of $\mu$ vary depending on the object to be measured. The values of $\mu$ for useful resin pieces are indicated respectively by $\mu_{OL}$ and $\mu_{OH}$. The value of k is set so that the term $-(\mu_L - k \cdot \mu_H)$ for useful resin pieces is zero. Then, the following formula (6) holds.

$$k = \mu_{OL}/\mu_{OH} \quad (6)$$

Accordingly, $-(\mu_L - k \cdot \mu_H)$ is $-\{\mu_L - (\mu_{OL}/\mu_{OH})\mu_H\}$. Thus, in the case where an object to be measured satisfies $\mu_L/\mu_H > \mu_{OL}/\mu_{OH}$, the slope of the change of differential value S with respect to thickness t is negative. In FIG. 4, this corresponds to the foreign material of small X-ray absorption. In the case where an object to be measured satisfies $\mu_L/\mu_H < \mu_{OL}/\mu_{OH}$, the slope of the change of differential value S with respect to thickness t is positive. In FIG. 4, this corresponds to the foreign material of large X-ray absorption.

The fact that the foreign material of small X-ray absorption satisfies the characteristic of $\mu_L/\mu_H > \mu_{OL}/\mu_{OH}$ means that in the case where the amount of absorption of a high energy X-ray by a useful resin piece is identical to that by the foreign material of small X-ray absorption, the foreign material of small X-ray absorption absorbs a greater amount a low energy X-ray than the useful resin piece. As described above, the foreign material of small X-ray absorption also contains elements with larger atomic numbers than the elements contained in the useful resin piece. Therefore, in the case where an object to be measured is irradiated with X-rays and its absorption of a range to which an X-ray sensor for the low energy X-ray responds is large and its absorption of a range to which an X-ray sensor for the high energy X-ray responds is small, the slope of the change of differential value S with respect to thickness t is negative.

On the contrary, the foreign material of large X-ray absorption satisfies the characteristic of $\mu_L/\mu_H < \mu_{OL}/\mu_{OH}$. This formula means that in the case where the amount of absorption of a low energy X-ray by a useful resin piece is identical to that by the foreign material of large X-ray absorption, the foreign material of large X-ray absorption absorbs a greater amount a high energy X-ray than the useful resin piece. The foreign material of large X-ray absorption contains elements with larger atomic numbers than the foreign material of small X-ray absorption, and elements with larger atomic numbers absorb X-rays of greater energy. Therefore, in the case where an object to be measured is irradiated with X-rays and its absorption of a range of X-ray energy to which an X-ray sensor for the high energy X-ray responds is large, the slope of the change of differential value S with respect to thickness t is positive.

The determination method for distinguishing foreign materials in the first embodiment is necessary in the case where the foreign materials contain a wide variety of elements. In order to avoid the erroneous determination due to differential value S, the determination particularly for objects to be measured in a range of large thicknesses t can be made based on the intensity of the transmitted low energy X-ray and then the determination can be made based on differential value S, to thereby increase the accuracy of sorting.

In the case of resin recycling for which resins to be recycled and foreign materials are to be differentiated from each other, foreign materials include resins containing 10 wt % or more of glass fibers and resins containing 1 to 10 wt % of a bromine-based flame retardant. Because waste plastics may contain a variety of elements such as silicon (Si), bromine (Br) as well as chlorine (Cl), calcium (Ca), titanium (Ti), zinc (Zn), antimony (Sb), and the like, the invention of the present embodiment is effective for increasing the accuracy of sorting.

It has been confirmed from the results of further experiments that even in the case where a chlorine-based resin such as vinyl chloride resin is to be removed as it is a foreign material, the object to be removed can be distinguished. As described above, the present invention has an advantage that one apparatus can be used to make a determination for sorting waste plastic pieces containing various additives. Further, the accuracy of sorting is improved, which makes it possible to improve the quality of reclaimed products without sacrificing the amount of reclaimed pieces.

Second Embodiment

In a second embodiment, in addition to the determination method described in connection with the first embodiment, a determination method is used for which Threshold Value 1, Threshold Value 2, and differential value parameter k are successively adjusted.

Figure 5:
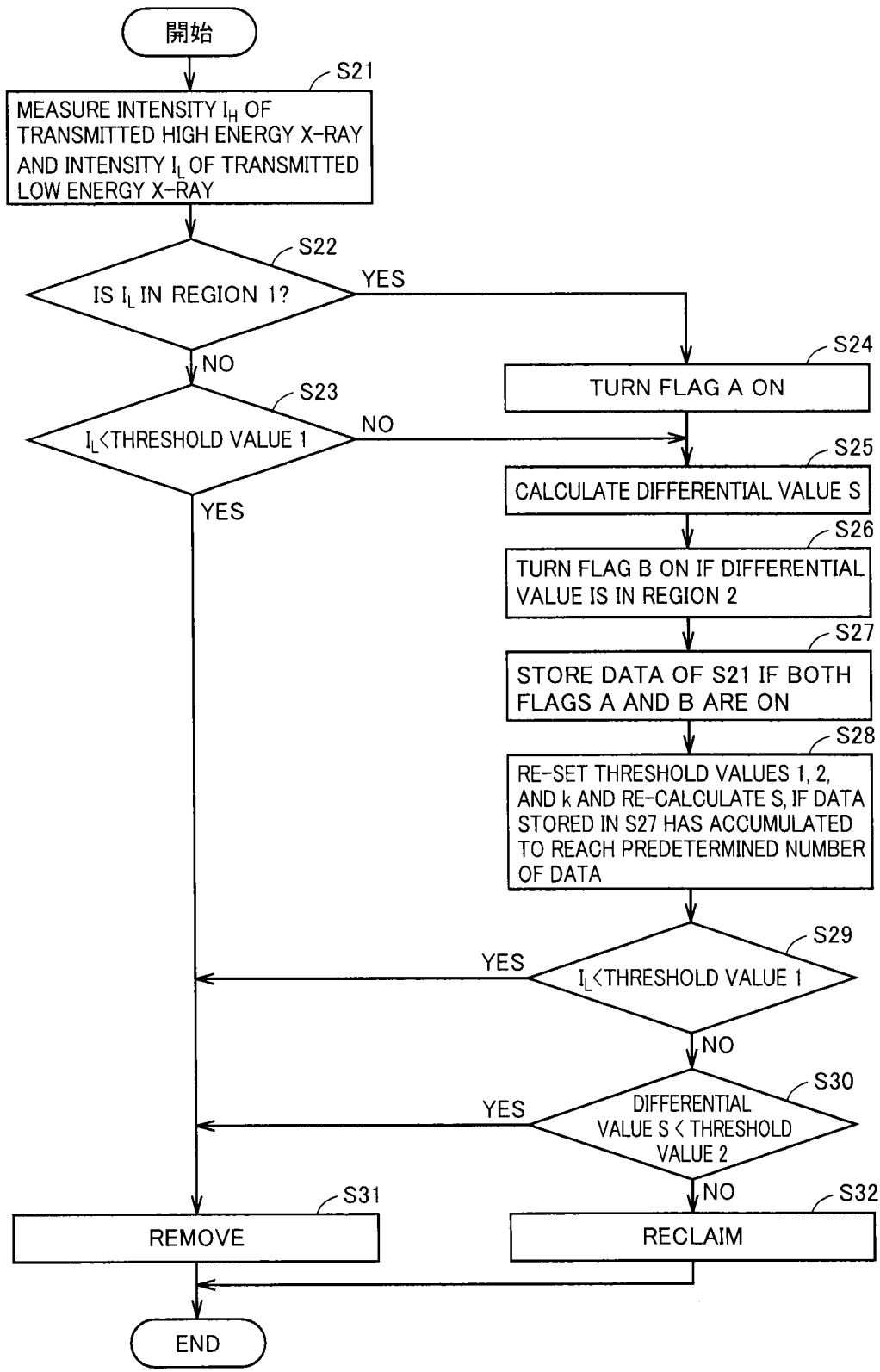
FIG. 5 is a determination flowchart for making a determination to distinguish between useful resin pieces and objects to be removed, in a second embodiment of the present invention.

FIG. 5 is a determination flowchart for making a determination to distinguish between useful resin pieces and objects to be removed in the second embodiment. Steps S21, S23, S25, and S30 correspond respectively to steps S11, S12, S13, and S14 in FIG. 1 described in connection with the first embodiment, and functions in the steps corresponding to each other are identical to each other.

According to the system of the second embodiment, a control device newly sets Region 1 of the intensity of the transmitted X-ray and Region 2 of differential value S in advance, in addition to Threshold Value 1, Threshold Value 2, and differential value parameter k used for the above-described determination. Region 1 is set as a range of the intensity of the transmitted low energy X-ray that useful resin pieces can take.

Figure 6:
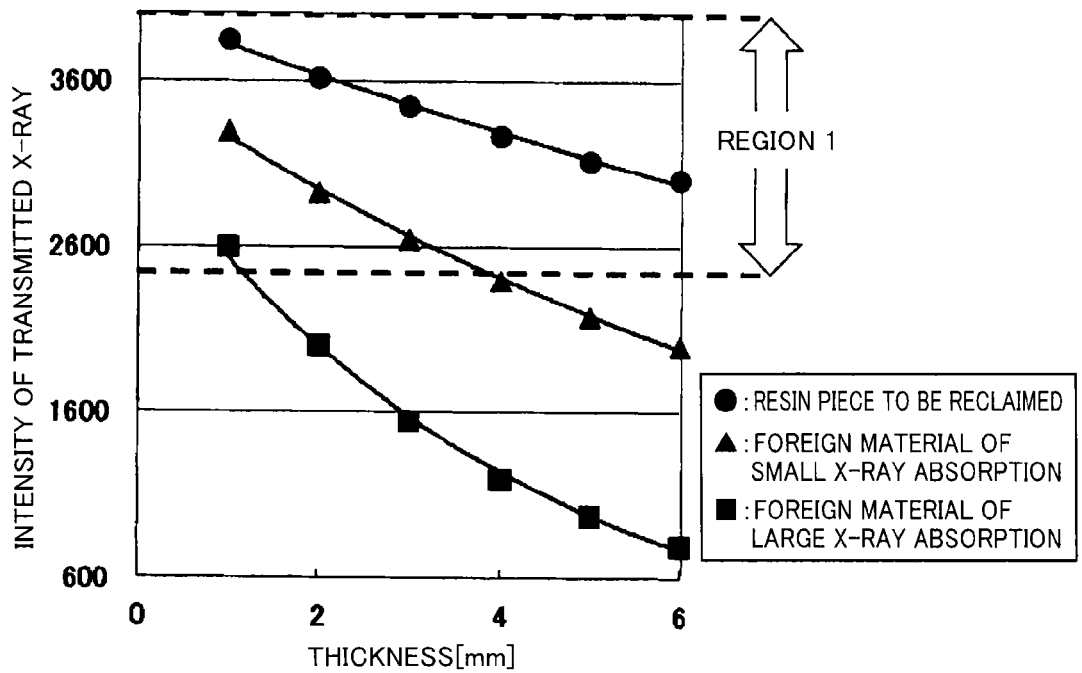
FIG. 6 is a diagram showing an example of Region 1 which is set for the intensity of a transmitted low energy X-ray, in the second embodiment of the present invention.

FIG. 6 is a diagram showing an example of Region 1 which is set for the intensity of a transmitted low energy X-ray, and indicates the range of Region 1 on the same graph as FIG. 2, using the region (the range indicated by the arrow) between two broken lines corresponding to the intensity of the transmitted X-ray. The range of Region 1 is provided for identifying resin pieces as useful resin pieces and is a reference similar to Threshold Value 1. Region 1, however, allows more resin pieces to be identified as useful resin pieces, than resin pieces identified as useful resin pieces based on Threshold Value 1. For example, it is desirable that the range is defined so that it includes useful resin pieces all the time even when the value of the intensity of the transmitted X-ray varies due to a factor such as the fact that resin pieces are different in composition from lot to lot in a line of a recycle plant. Further, as will be described later herein, Region 1 is not used as a reference for sorting resin pieces.

Figure 7:
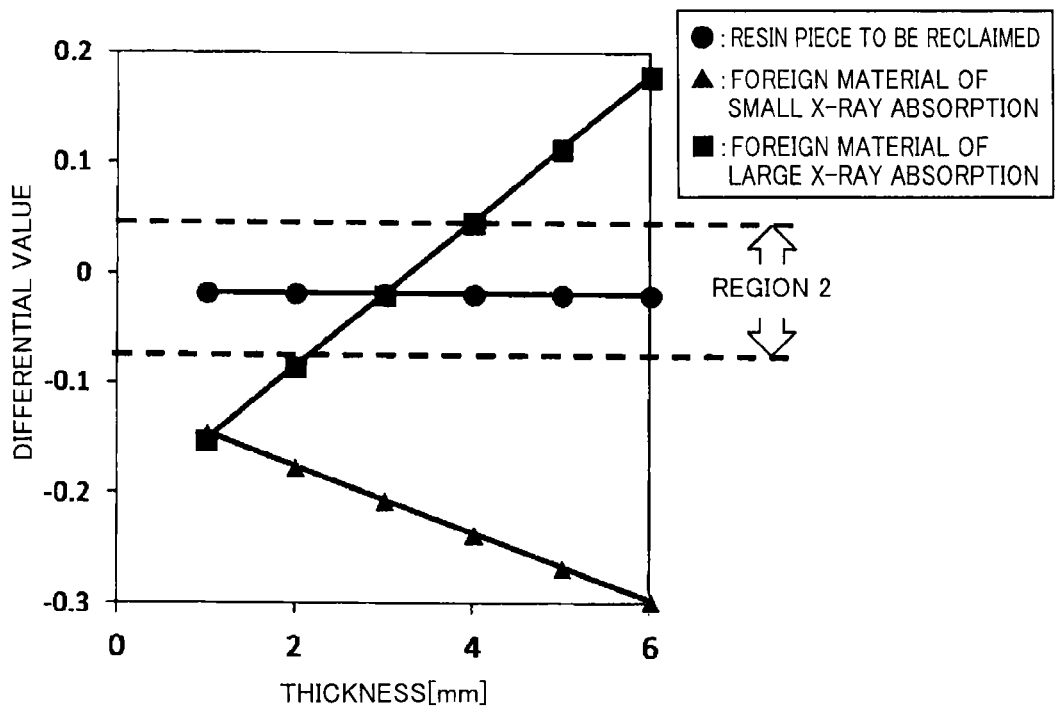
FIG. 7 is a diagram showing an example of Region 2 which is set for the differential value, in the second embodiment of the present invention.

Further, Region 2 is set as a range of the differential value that useful resin pieces can take. FIG. 7 is a diagram showing an example of Region 2 which is set for the differential value, and indicates an example of set Region 2 on the same graph as FIG. 4. Like Region 1, Region 2 allows more resin pieces to be identified as useful resin pieces, than resin pieces identified as useful resin pieces based on Threshold Value 2. The results of the determinations as to whether or not the resin pieces are included in Region 1 and Region 2 are used for the successive adjustments of Threshold Value 1, Threshold Value 2, and differential value parameter k.

Next, the operations in the steps of FIG. 5 will be described.

In step S21, an X-ray irradiation unit irradiates an object to be measured with a low energy X-ray and a high energy X-ray having respective energy ranges different from each other, and respective intensities $I_H$, $I_L$ of the transmitted X-rays are acquired by an X-ray sensor.

In step S22, a control device confirms whether or not intensity $I_L$ of the transmitted X-ray, which is used to be compared with Threshold Value 1 in S23, is a value included in the range of Region 1 set in advance. When intensity $I_L$ of the transmitted X-ray is a value included in Region 1 (YES in S22), the process proceeds to step S24.

In step S24, the control device turns Flag A ON. After this, the process proceeds to step S25. It should be noted that the control device used for the present embodiment includes a storage unit for storing the above-described measured values and set values. When it is determined in step S22 that intensity $I_L$ of the transmitted X-ray is not within Region 1, the process proceeds to step S23.

In step S23, the control device performs the first determination step by making a comparison between intensity $I_L$ of the transmitted X-ray and Threshold Value 1. In step S23, when it is determined that intensity $I_L$ of the transmitted X-ray is equal to or more than Threshold Value 1, the process proceeds to step S25 and, when it is determined that intensity $I_L$ of the transmitted X-ray is less than Threshold Value 1, the process proceeds to step S31.

In step S25, the control device calculates a differential value S based on the energy subtraction method, from intensity $I_L$ of the transmitted low energy X-ray and intensity $I_H$ of the transmitted high energy X-ray that are obtained in step S21.

In step S26, the control device confirms whether or not the obtained differential value is a value included in the range of Region 2 which is set in advance and, when the differential value is a value included in Region 2, the control device turns Flag B ON.

In step S27, as both Flag A and Flag B are ON, the control device stores the values measured in S21 in the storage unit in the form of an array. This is for the reason that the probability that the resin piece is a useful resin piece is high in the case where both Flag A and Flag B are ON.

In step S28, the control device uses the data stored in S27 to re-set Threshold Value 1, differential value parameter k, and Threshold Value 2.

In step S29, the control device performs again the first determination step by making a comparison between intensity $I_L$ of the transmitted X-ray and Threshold Value 1. In step S29, when it is determined that intensity $I_L$ of the transmitted X-ray is equal to or more than Threshold Value 1, the process proceeds to step S30 and, when it is determined that intensity $I_L$ of the transmitted X-ray is less than Threshold Value 1, the process proceeds to step S31.

In step S30, the control device performs the second determination step by making a comparison between differential value S for the object to be measured and Threshold Value 2. When the result of the comparison by the control device between differential value S for the object to be measured and Threshold Value 2 indicates that differential value S for the object to be measured is less than Threshold Value 2 (YES in S30), the process proceeds to step S31. When differential value S for the object to be measured is equal to or more than Threshold Value 2 (NO in S30), the process proceeds to step S32.

In step S31, the control device determines that the object to be measured is an object to be removed.

In step S32, the control device determines that the object to be measured is a useful resin piece.

Here, a detailed description is given of how to re-set Threshold Value 1, differential value parameter k, and Threshold Value 2. The re-setting in S28 is done based on the data stored in S27 for a plurality of objects to be measured. As for the timing at which the re-setting is done, the re-setting may be done at the time when the data stored in S27 accumulate to reach the number of data set in advance, such as the data corresponding to 1000 objects to be measured, or may be done successively for each determination using the data corresponding to the current object to be measured and the number of objects preceding the current object where the number is set in advance. In any case, unless a certain number of data stored in step S27 has accumulated, the operation in step S28 is not performed.

Figure 8:
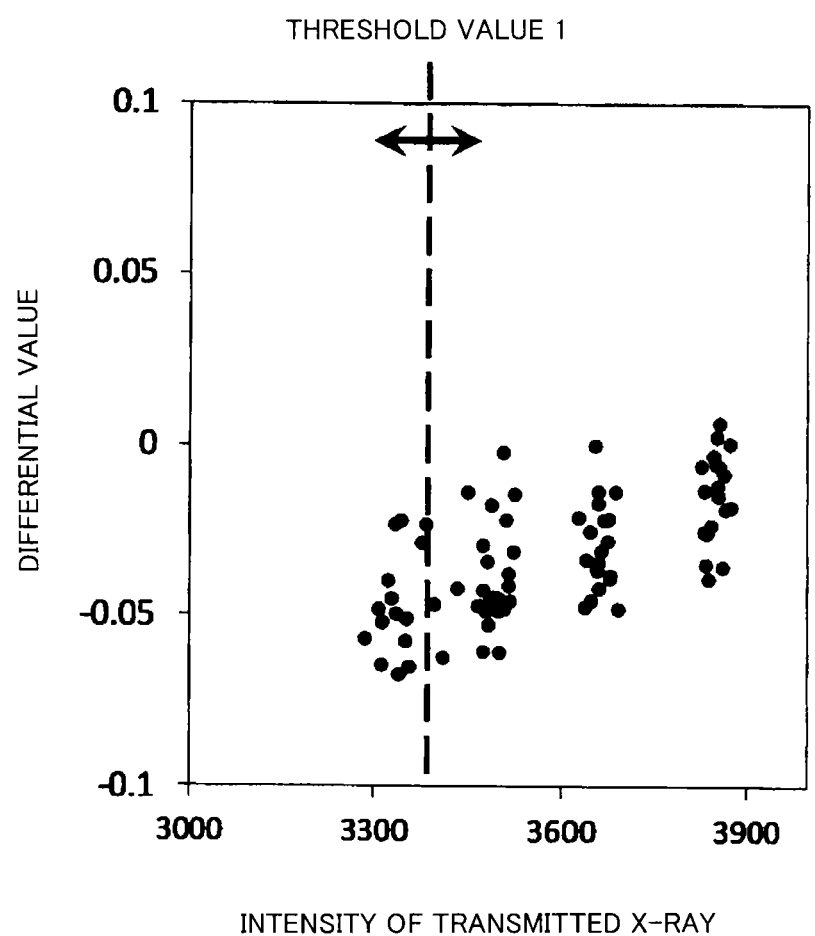
FIG. 8 is a diagram showing a method of adjusting Threshold Value 1 for the intensity of a transmitted low energy X-ray, in the second embodiment of the present invention.

FIG. 8 is a diagram for illustrating a method of adjusting Threshold Value 1 for the intensity of the transmitted low energy X-ray. In FIG. 8, the values which are measured using samples of polypropylene resin pieces as useful resin pieces are plotted on the graph having the horizontal axis representing the intensity of the transmitted X-ray and the vertical axis representing the differential value.

The values taken by the useful resin pieces are sparsely distributed in the graph, because of differences between the resin pieces. Threshold Value 1 is adjusted with respect to the values on the horizontal axis in FIG. 8. Namely, Threshold Value 1 can be increased/decreased (moved rightward/ leftward in FIG. 8) to thereby adjust the ratio of the number of data which is Threshold Value 1 or more to the total number of data. For example, Threshold Value 1 can be adjusted so that all resin pieces provide the intensity of the transmitted X-ray higher than Threshold Value 1, to thereby select the maximum yield. In contrast, Threshold Value 1 can be set so that a certain ratio of data is lower than Threshold Value 1 to thereby enhance the quality of the useful resin pieces.

As a specific example of the method of automatically adjusting Threshold Value 1 by a calculation, a method of setting a ratio of erroneous determinations which is the ratio of erroneous determinations of identifying useful resin pieces as objects to be removed will be described. For example, if the ratio of erroneous determinations is set to 1%, the threshold value is set so that the number of data smaller than Threshold Value 1 is 1%, with respect to the data of the intensity of the transmitted X-ray included in Region 1. In the case where the ratio of erroneous determinations is set to 0%, Threshold Value 1 is set to the minimum value among the data of the intensity of the transmitted X-ray in Region 1. Beside this, an example of the method of automatically adjusting Threshold Value 1 based on a calculation may be a method according to which Threshold Value 1 is set to a value smaller by a certain value (a value of 50 to 100 for example) than the minimum value of the intensity of the transmitted X-ray for the useful resin pieces as shown in FIG. 8, to provide a tolerance on the accuracy of the determination, for example.

On the contrary, in order to lower the ratio of erroneous determinations of identifying useful resin pieces as objects to be removed, Threshold Value 1 can be set to a value larger by a certain value (a value of 50 to 100 for example) than the minimum value of the intensity of the transmitted X-ray.

In this way, while many data are stored in consideration of the measurement error of the value of the intensity of the transmitted X-ray, Threshold Value 1 can be adjusted as appropriate to manage the quality of sorted objects in real time.

Next, re-setting of differential value parameter k will be described. FIG. 9 is a diagram showing a relation between intensity $I_L$ of the transmitted low energy X-ray and the differential value, for illustrating automatic adjustment of differential value parameter k.

Figure 9A:
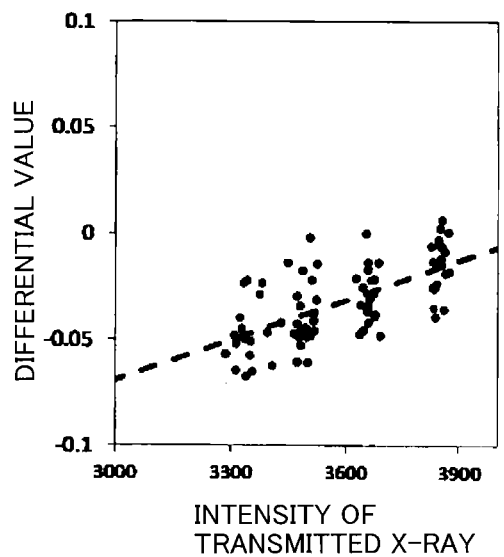
FIG. 9A is a diagram showing a relation between the intensity of a transmitted low energy X-ray and a differential value for illustrating automatic adjustment of a differential value parameter, in the second embodiment of the present invention.
Figure 9B:
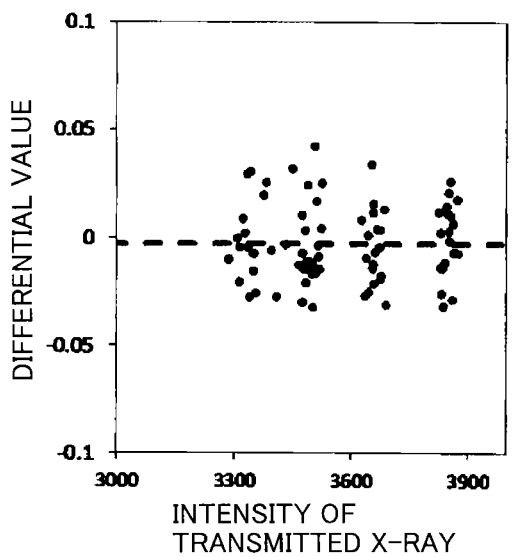
FIG. 9B is a diagram showing a relation between the intensity of a transmitted low energy X-ray and a differential value for illustrating automatic adjustment of a differential value parameter in a state where the differential value parameter has been re-set.

In FIG. 9A, an approximation straight line calculated from the same points of the data as those used in FIG. 8 is represented by a broken line. FIG. 9B shows a state where the differential value parameter has been re-set. The differential value parameter is an optimum value when the values of the vertical axis in the graph for useful resin pieces are close to zero. Therefore, it is desirable that the approximation straight line is flat in the vicinity of zero, like FIG. 9B. Thus, the approximation straight line is calculated for values plotted in the graph having the horizontal axis representing the intensity of the transmitted X-ray and the vertical axis representing the differential value, to find an optimum value of differential value parameter k that provides the slope of the approximation straight line which is closest to zero. Accordingly, the differential value parameter can automatically be adjusted.

Here, a specific method for automatically re-setting differential value parameter k will be described. The geometric mean of all intensities of the transmitted low energy X-ray that have been stored is calculated. Likewise, the geometric mean of the intensities of the transmitted high energy X-ray that have been stored in the aforementioned storage unit is calculated. Each of the geometric means is divided by the value of the intensity of the transmitted X-ray on the condition that there is no object to be measured, and thereafter respective natural logarithms of them are taken.

The differential value parameter is re-set to a value determined by dividing the value calculated from the intensities of the transmitted low energy X-ray, by the value calculated from the intensities of the transmitted high energy X-ray. The re-set differential parameter value k is calculated according to the following formula (7), where $I_{LGM}$ is the geometric mean of the intensities of the transmitted low energy X-ray, is the geometric mean of the intensities of the transmitted high energy X-ray, and $I_0$ is the intensity of the transmitted X-ray on the condition that there is no object to be measured.

$$k = \log_e(I_{LGM}/I_0)/\log_e(I_{HGM}/I_0) \tag{7}$$

Figure 10:
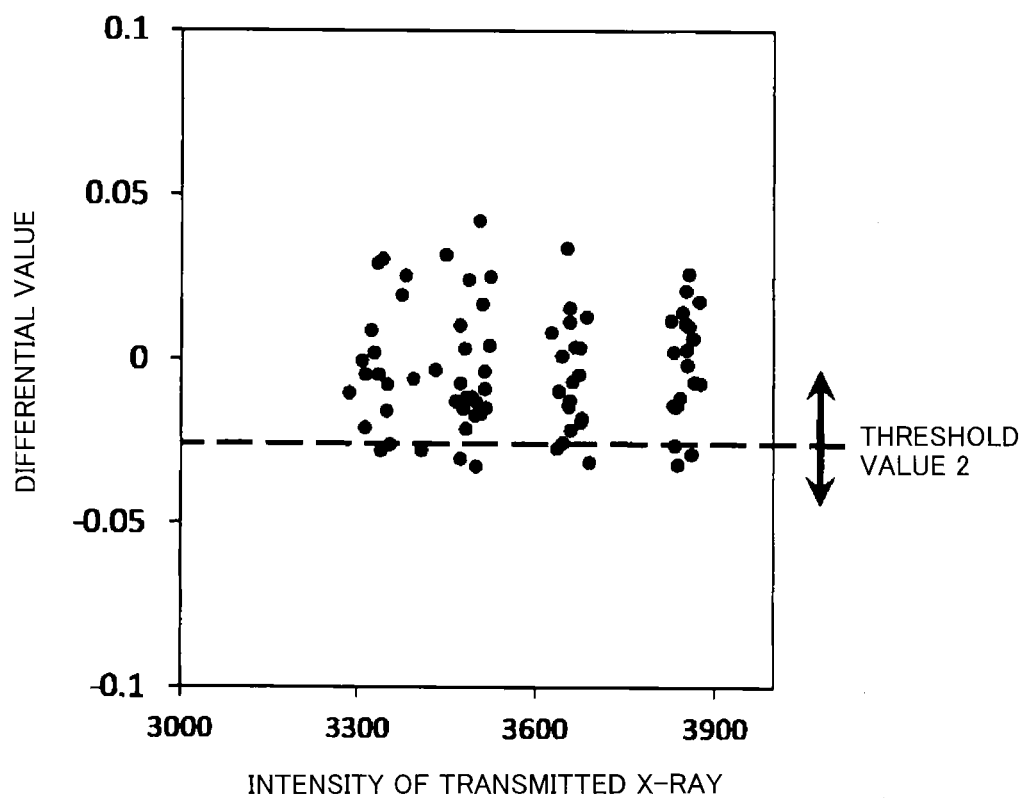
FIG. 10 is a diagram showing a relation between the intensity of a transmitted low energy X-ray and a differential value for illustrating automatic adjustment of a differential value parameter, in the second embodiment of the present invention.

Next, the stored values of the intensity of the transmitted X-ray and the re-set differential value parameter k are used to re-set Threshold Value 2. FIG. 10 is a diagram for illustrating a relation between the intensity of the transmitted low energy X-ray and the differential value, and the method of re-setting Threshold Value 2. FIG. 10 shows the same data as FIG. 9B. For each of the stored intensities of the transmitted X-ray, the differential value is re-calculated using the re-set differential value parameter k. After this re-calculation, Threshold Value 2 is adjusted in a similar manner to the re-setting of Threshold Value 1. The method of automatically adjusting Threshold Value 2 may be, like the method for Threshold Value 1, a method according to which the ratio of allowable erroneous determinations is set in advance and Threshold Value 2 is set so that the ratio of the allowable erroneous determinations is satisfied, or Threshold Value 2 may be set to a value with a margin in terms of the minimum value of the differential value.

As seen from the foregoing, Region 1 and Region 2 can be set so that only a certain ratio of objects is to be removed to increase the yield, for example, rather than determining that all objects, which have been identified as objects to be removed with respect to Threshold Value 1 and Threshold Value 2, should be removed. Thus, the values can be set to values beyond those that useful resin pieces can take.

Moreover, in such a case where the distribution of materials for objects to be measured varies from time to time or from day to day, the method of the second embodiment that makes successive adjustments of the threshold values and the differential value parameter can suppress the influence of the material variation on the accuracy of the determination. Particularly in the case where resin pieces into which waste plastics are crushed are to be measured, the characteristics distribution of not only objects to be removed but also useful resin pieces to be reclaimed is not uniformly controlled, and therefore, the above-described determination method can be used to improve the accuracy of the determination.

Third Embodiment

A third embodiment relates to a foreign material determination method that enables sorting with higher accuracy by separately obtaining information about the thickness of the object to be measured and feeding back the information to be used for determination, in addition to performing the determination methods of the first and second embodiments. The following description will be given as an additional description to the description of the first embodiment.

Figure 11:
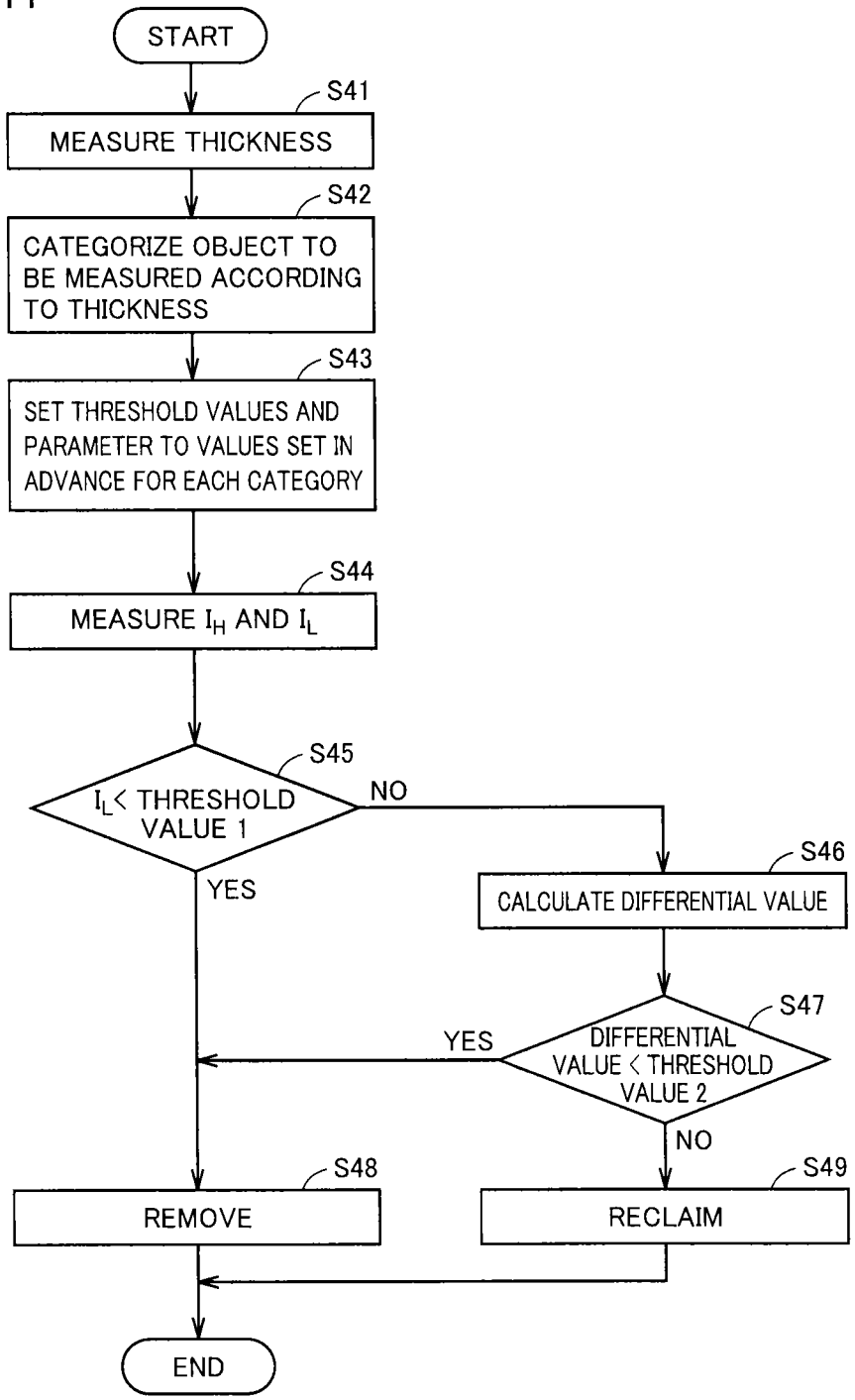
FIG. 11 is a determination flowchart for making a determination to distinguish between useful resin pieces and objects to be removed, in a third embodiment of the present invention.

FIG. 11 is a determination flowchart for making a determination to distinguish between useful resin pieces and objects to be removed in the third embodiment. As compared with FIG. 1, step S44 corresponds to step S11, step S45 corresponds to step S12, step S46 corresponds to step S13, and step S47 corresponds to step S14.

First, in step S41, the thickness of an object to be measured is measured with a laser-type thickness gauge or the like.

Figure 12:
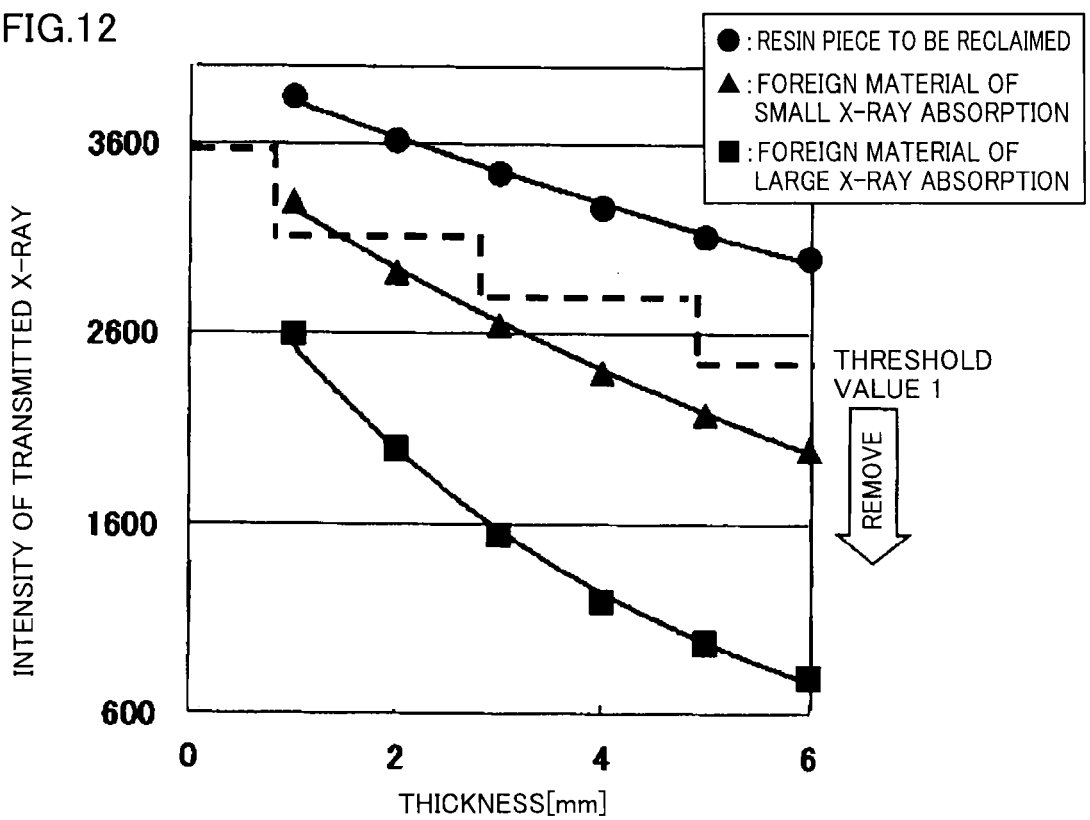
FIG. 12 is a diagram showing a relation between the intensity of a transmitted low energy X-ray and the thickness of a resin piece, in the third embodiment of the present invention.

In step S42, the object to be measured is categorized according to the measured thickness. An object to be measured is categorized into any one of a plurality of categories defined in advance, in such a manner for example that an object having a thickness of less than 1 mm is categorized into T1, and an object having a thickness of not less than 1 mm and less than 3 mm is categorized into T2. For each category, Threshold Value 1, Threshold Value 2, and the value of the differential value parameter which are used in the flowchart of FIG. 1 are set in advance, to thereby enable these values to be assigned according to the thickness of the object to be measured. FIG. 12 is a diagram showing a relation between the intensity of the transmitted low energy X-ray and the thickness of a resin piece. In FIG. 12, Threshold Value 1 indicated by the broken line has different values corresponding respectively to the categories and is therefore represented by a step-like function with respect to the thickness.

As described above in connection with the first embodiment, differential value S based on the energy subtraction method for useful resin pieces is a value defined regardless of the thickness of the resin piece. In contrast, differential value S for objects to be removed varies depending on the thickness of the object. Further, as described above in connection with the second embodiment, the differential value for useful resin pieces also varies depending on the resin pieces. Therefore, like Threshold Value 1, different Threshold Values 2 can be set for different categories of the thickness, respectively, to thereby tolerate the variation depending on the useful resin pieces, particularly thick resin pieces, and increase the yield of useful resin pieces.

Figure 13:
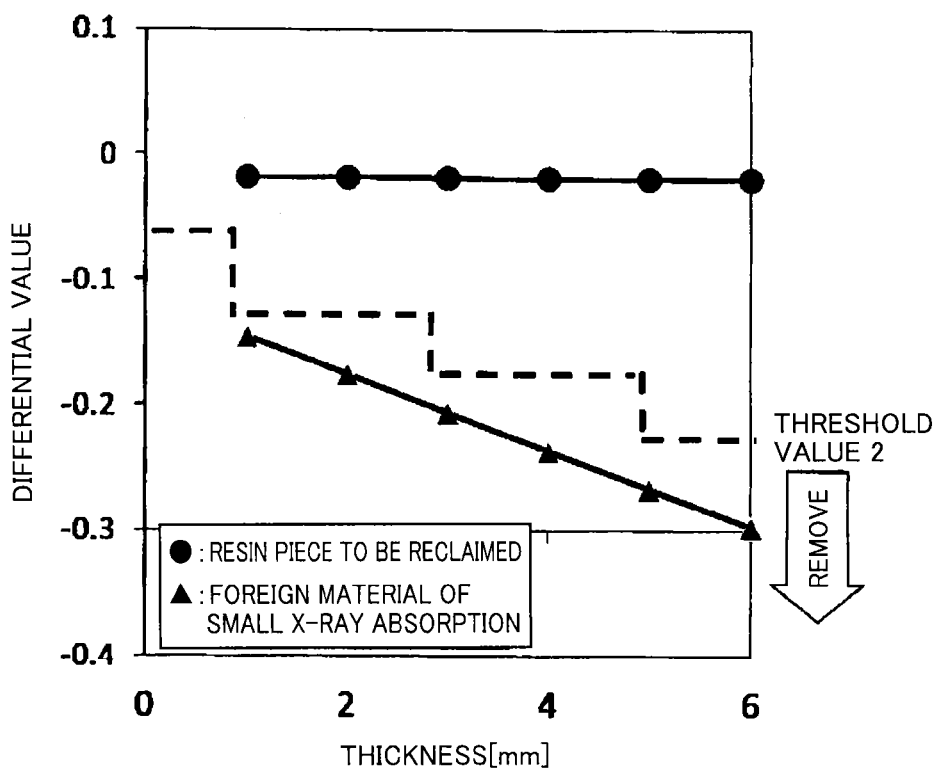
FIG. 13 is a diagram showing a relation between differential value S and the thickness of a resin piece, in the third embodiment of the present invention.

FIG. 13 is a diagram showing a relation between the differential value and the thickness of a resin piece, in the case where Threshold Value 2 is set according to the thickness of an object to be measured. For the sake of easy understanding, only the values are shown for useful resin pieces and foreign materials of small X-ray absorption, and the values are also plotted for foreign materials in the region used in the first determination step for distinguishing materials to be removed. Here, as described above, the differential value for useful resin pieces is defined regardless of the thickness, and therefore, Threshold Value 2 may be set constant regardless of the thickness. The extent of one thickness category depends on the time taken for measuring one object to be measured, and the accuracy of the thickness measurement. If the objects to be measured are uniform in thickness and can be measured with an accuracy so that an error is 0.1 mm or less, foreign materials can be distinguished by only the measurement based on the intensity of the transmitted X-ray without using the differential value. In the case where resin pieces into which parts are crushed are applied as objects to be measured, however, the resin pieces are not uniform in thickness. The present invention has been made to address this condition. In the third embodiment, the thickness can be measured prior to the X-ray inspection step to perform accurate sorting even the objects vary to a large extent in thickness.

In step S43, according to the category determined in step S42, the control device selects Threshold Value 1, Threshold Value 2, and differential value parameter k. As to Threshold Value 1, for example, the control device selects Threshold Value 1-1 for category T1 of the objects to be measured, and selects Threshold Value 1-2 for category T2 of the objects to be measured (not shown). As to Threshold Value 2, for example, the control device selects Threshold Value 2-1 for category T1 of the objects to be measured, and Threshold Value 2-2 for category T2 of the objects to be measured (not shown). As to the differential value parameter, the control device selects k1 for category T1 of the objects to be measured, and k2 for category T2 of the objects to be measured (not shown).

The operations of subsequent steps S44 to S49 are similar to those of steps S11 to S14, S31, and S32, and thus the description thereof will not be repeated.

As to step S44 and its subsequent steps in the procedure of determination shown in FIG. 11, the procedure of determination in FIG. 5 illustrated above in connection with the second embodiment can also be used. In this case, the intensities of the transmitted X-ray are stored in S27 in different regions depending on the categories determined in S42.

When Threshold Value 1, Threshold Value 2, and the differential value parameter are re-set in S28, the data used for calculation for re-setting is only the values in the same category. The control device uses, for example, data in category Ti of the thickness of resin piece 3, to calculate Threshold Value 1-$i$, Threshold Value 2-$i$, and differential value parameter ki.

As shown in FIG. 2, the intensity of the transmitted X-ray varies depending on the thickness of the object to be measured. As shown in FIG. 4, the differential value for the object to be removed also varies depending on the thickness. Therefore, the determination method of the third embodiment can be introduced to suppress the influences of the variation depending on the useful resin pieces or the objects to be removed and thus improve the accuracy of determination for sorting.

Fourth Embodiment

Regarding a fourth embodiment of the present invention, a description will be given of a sorting apparatus capable of speedily sorting useful resin pieces from a large amount of waste plastic pieces including objects identified as foreign materials to be removed, using the determination method described above in connection with the first embodiment.

Figure 14:
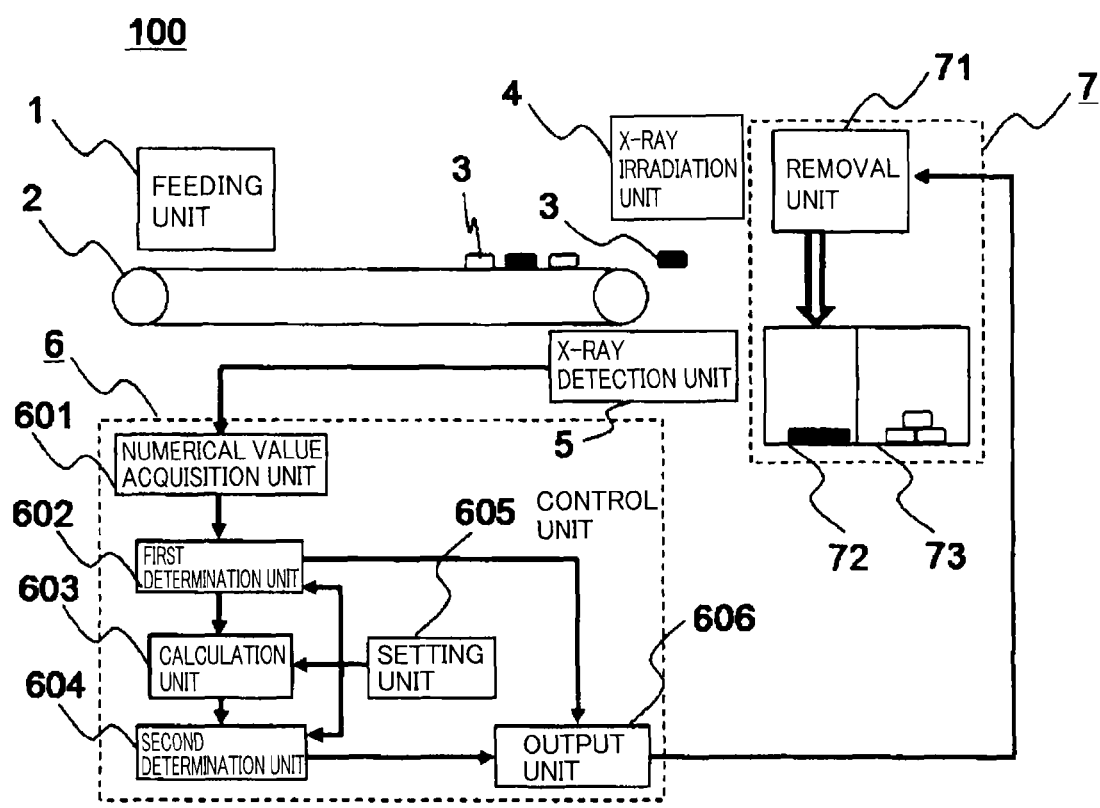
FIG. 14 is a diagram schematically showing a configuration of a sorting apparatus according to a fourth embodiment of the present invention.

FIG. 14 is a diagram schematically showing a configuration of a sorting apparatus according to the fourth embodiment of the present invention. Sorting apparatus 100 includes a feeding unit 1 feeding resin pieces 3 of waste plastic to a conveying unit 2, an X-ray irradiation unit 4 irradiating resin piece 3 with an X-ray, an X-ray detection unit 5 detecting the X-ray transmitted through resin piece 3, a control unit 6, and a sorting unit 7 sorting a resin piece.

Next, an operation of sorting apparatus 100 will be described in detail.

First, feeding unit 1 formed of a hopper and a feeder feeds resin pieces 3, which are objects to be measured, onto conveying unit 2 formed of a belt conveyor or the like. Conveying unit 2 may be a simple slider or runway. Resin pieces 3 are a mixture of useful resin pieces and objects to be removed. Resin piece 3 conveyed by conveying unit 2 is irradiated with an X-ray under X-ray irradiation unit 4 which is placed above and downstream of conveying unit 2 and formed of an X-ray source. The X-ray transmitted through resin piece 3 is detected by X-ray detection unit 5 which is placed directly below X-ray irradiation unit 4 and formed of a dual energy X-ray sensor. This dual energy X-ray sensor is a linear sensor whose width is equivalent to that of conveying unit 2, and is capable of detecting respective intensities of the X-ray at a plurality of points on a line, by means of a plurality of pixels. Resin pieces 3 may therefore be conveyed on conveying unit 2 in the state of being arranged in the direction perpendicular to the direction in which the resin pieces are conveyed. Resin piece 3 is released from conveying unit 2 into the air and passed through the space between X-ray irradiation unit 4 and X-ray detection unit 5. A signal detected by X-ray detection unit 5 is transmitted to control unit 6. Control unit 6 determines whether resin piece 3 is a useful resin piece or an object to be removed.

Here, the determination by control unit 6 will be described in detail. The procedure of the determination is the procedure of the flowchart shown in FIG. 1. Since X-ray detection unit 5 can use a plurality of linearly arranged pixels to simultaneously acquire intensities of the X-ray at a plurality of points, the procedure of the determination described below applies to a process which can independently be performed on measurement data for each pixel of X-ray detection unit 5. First, a numerical value acquisition unit 601 acquires, from the data acquired by X-ray detection unit 5, intensity $I_L$ of a transmitted low energy X-ray and intensity $I_H$ of a transmitted high energy X-ray. When numerical value acquisition unit 601 acquires the numerical value data, a smoothing process or the like for reducing noise may separately be added.

A first determination unit 602 compares acquired intensity $I_L$ of the transmitted low energy X-ray with Threshold Value 1 set by a setting unit 605. When intensity $I_L$ of the transmitted low energy X-ray is smaller than Threshold Value 1, first determination unit 602 determines that resin piece 3 is an object to be removed, and transmits a signal to an output unit 606. The method of setting Threshold Value 1 is the one as described above in connection with the first embodiment.

When first determination unit 602 does not determine that resin piece 3 is an object to be removed, first determination unit 602 transmits the numerical values acquired by numerical value acquisition unit 601 to a calculation unit 603. Based on the transmitted numerical values and differential value parameter k which is set in advance by setting unit 605, calculation unit 603 calculates differential value S using formula (5), and transmits the result to a second determination unit 604.

Second determination unit 604 compares the differential value sent from calculation unit 603 with Threshold Value 2 set in advance by setting unit 605. When the result of this comparison is that the differential value obtained by the calculation by calculation unit 603 is smaller than Threshold Value 2, second determination unit 604 determines that resin piece 3 is an object to be removed, and transmits a signal to output unit 606. When differential value S is Threshold Value 2 or more, second determination unit 604 determines that resin piece 3 is a useful resin piece, and does not transmit the signal to output unit 606. When the signal is transmitted from first determination unit 602 or second determination unit 604, output unit 606 transmits a removal signal to sorting unit 7.

Sorting unit 7 is made up of a removal unit 71 formed of an air gun or the like for blowing off resin piece 3 with compressed air when the removal signal is transmitted from output unit 606, a removal box 72 for collecting objects to be removed which are sorted and removed by the air gun, and a reclaim box 73 for reclaiming resin piece 3 released into the air from conveying unit 2 without sorted and removed by the air gun.

When it is determined as a result of the determination by control unit 6 that resin piece 3 is an object to be removed, the signal is transmitted from output unit 606 to the air gun of removal unit 71, after resin piece 3 is passed in the air above X-ray detection unit 5, compressed air is emitted from the air gun, and resin piece 3 is blown into removal box 72.

When control unit 6 determines that resin piece 3 is a useful resin piece, the signal is not transmitted from output unit 606 and the air gun of removal unit 71 is not operated. Therefore, resin piece 3 identified as a useful resin piece is collected into reclaim box 73 through the same trajectory as the one along which resin piece 3 is released from conveying unit 2 into the air.

The above-described method is appropriate for the case where the number of useful resin pieces to be reclaimed is larger than the number of objects to be removed, among the whole objects to be measured. On the contrary, when the number of objects to be removed is larger than the number of useful resin pieces to be reclaimed, high-pressure air may be applied to the useful resin pieces for sorting them.

Control unit 6 uses the numerical value for each of pixels included in X-ray detection unit 5 to determine whether resin piece 3 is a useful resin piece or an object to be removed. Thus, even when the rate at which resin piece 3 is conveyed by conveying unit 2 is set to a high rate of 50 m/min to 100 m/min, sorting can be done without deteriorating the accuracy of determination. Further, the determinations can be made in the two stages by first determination unit 602 and second determination unit 604 to automatically and speedily sort a large amount of objects, by means of the configuration of the apparatus like the fourth embodiment, without determination based on an image by a person, even when objects to be removed are a mixture of resin pieces including an additive containing a Si, and resin pieces including an additive containing an element like Br with its atomic number away from that of Si by 10 or more.

It should be noted that instead of transmitting the removal signal when it is determined that the object is an object to be removed, a sorting signal may be transmitted for sorting a useful resin piece, or a system operated by using both the removal signal and the sorting signal may be used.

Fifth Embodiment

Regarding a fifth embodiment, a description will be given of a sorting apparatus 100a capable of automatically sorting resins to be recycled from foreign materials that enables the set values used for the determination to be changed automatically as described above in connection with the second embodiment.

Figure 15:
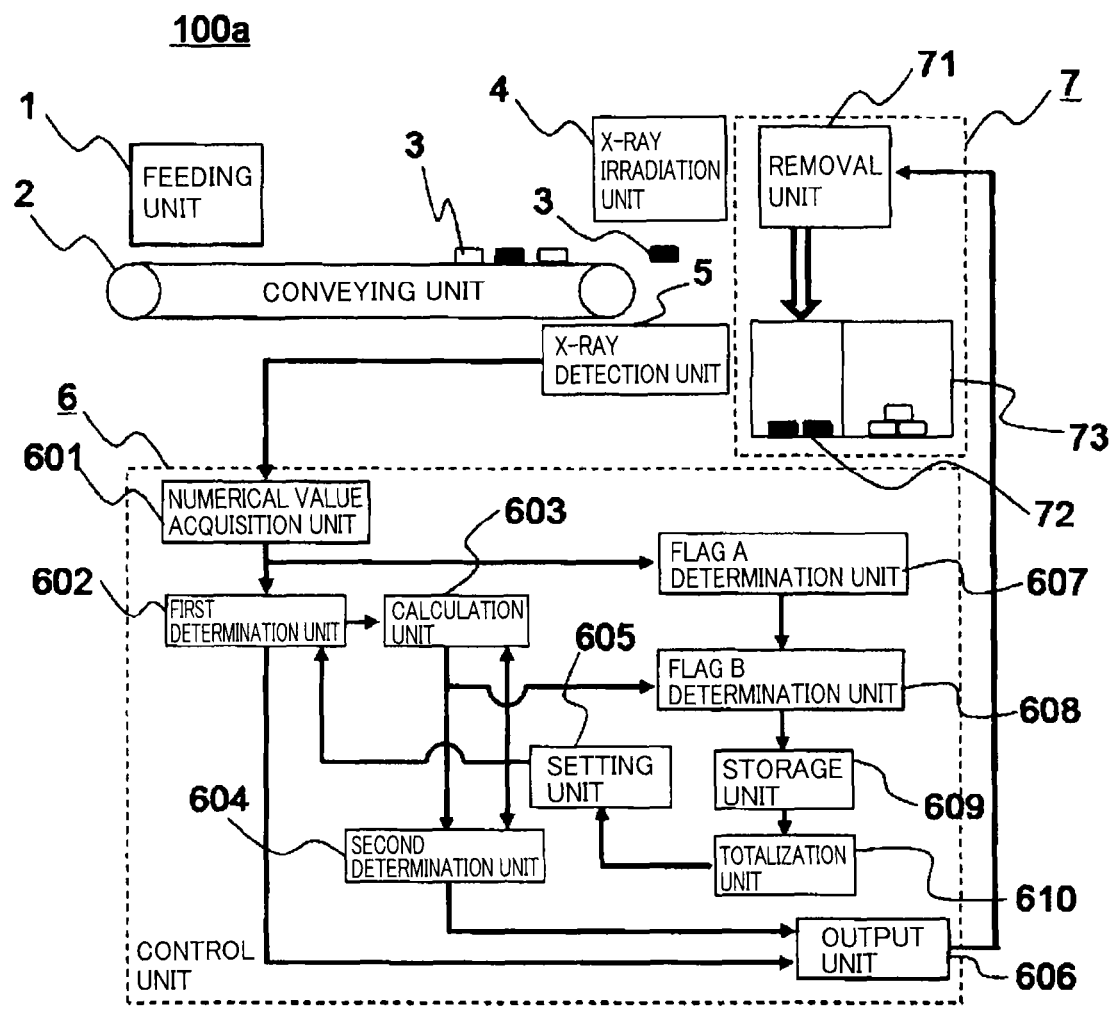
FIG. 15 is a diagram schematically showing a configuration of a sorting apparatus according to a fifth embodiment of the present invention.

FIG. 15 is a diagram schematically showing a configuration of sorting apparatus 100a according to the fifth embodiment. The same part of the apparatus as that shown in FIG. 14 is denoted by the same numeral. The flow from conveying resin piece 3 to measuring by X-ray detection unit 5, and the flow to the automatic sorting in response to the signal which is output from output unit 606 are identical to those of the fourth embodiment. Therefore, a determining operation by control unit 6 different from that of the fourth embodiment will be described. The fifth embodiment is directed to an apparatus capable of appropriately and automatically adjusting/changing Threshold Value 1, Threshold. Value 2, and differential value parameter k that are parameters used for making a determination to distinguish useful resin pieces. The procedure of the determination for distinguishing useful resin pieces from objects to be removed is the one as indicated by the flowchart shown in FIG. 5.

After numerical value acquisition unit 601 acquires the intensity of the transmitted low energy X-ray and the intensity of the transmitted high energy X-ray, acquisition unit 601 transmits this data to first determination unit 602 and simultaneously to a Flag A determination unit 607. Flag A determination unit 607 determines whether or not the intensity of the transmitted low energy X-ray is included in Region 1 which is set in advance as a range of values that useful resin pieces can take. When the intensity of the transmitted low energy X-ray is included in Region 1, Flag A determination unit 607 transmits the result of determination and the intensity of the transmitted X-ray to a Flag B determination unit B. When first determination unit 602 makes the determination in first stage and then determines that resin piece 3 is an object to be removed, first determination unit 602 transmits the removal signal to output unit 606.

Regardless of the result of the determination in the first stage by first determination unit 602, calculation unit 603 calculates the differential value. The result of calculation of the differential value is transmitted to Flag B determination unit 608. When first determination unit 602 does not determine that the resin piece is an object to be removed, the result of calculation of the differential value is also transmitted to second determination unit 604. When it is determined as a result of determination in the second stage by the second determination unit that resin piece 3 is an object to be removed, the removal signal is transmitted to output unit 606 like the one shown in FIG. 14. Only when Flag B determination unit 608 receives the signal from Flag A determination unit 607, Flag B determination unit 608 receives the differential value which is the result of calculation by calculation unit 603. After this, Flag B determination unit 608 determines whether or not the differential value is included in a range of Region 2 which is set in advance as a range of values that useful resin pieces can take. When the differential value is included in Region 2, Flag B determination unit 608 transmits the intensity of the transmitted low energy X-ray and the intensity of the transmitted high energy X-ray received from the Flag A determination unit, to a storage unit 609.

The values of the intensity of the transmitted X-ray for a plurality of resin pieces 3 are accumulated in storage unit 609. A totalization unit 610 re-calculates Threshold Value 1, Threshold Value 2, and differential value parameter k which are parameters used for determination, based on accumulated data of a certain number or more. The method of setting these three parameters is the one as described above in connection with the second embodiment. The parameters re-calculated by totalization unit 610 are transmitted to setting unit 605 for making a determination for the subsequent resin piece 3.

Like the fifth embodiment, the sorting apparatus having a mechanism of re-setting the parameters for making a determination can be used to achieve prevention of deterioration in the accuracy of distinguishing foreign materials, due to variation from time to time or variation from day to day of fed resin pieces 3, in addition to the effects of the fourth embodiment.

Sixth Embodiment

Regarding a sixth embodiment, a description will be given of a sorting apparatus 100b capable of automatically sorting useful resin pieces from objects to be removed, based on the result of measurement of the thickness of the object to be measured and the result of measurement of the intensity of the transmitted X-ray as described above in connection with the third embodiment.

Figure 16:
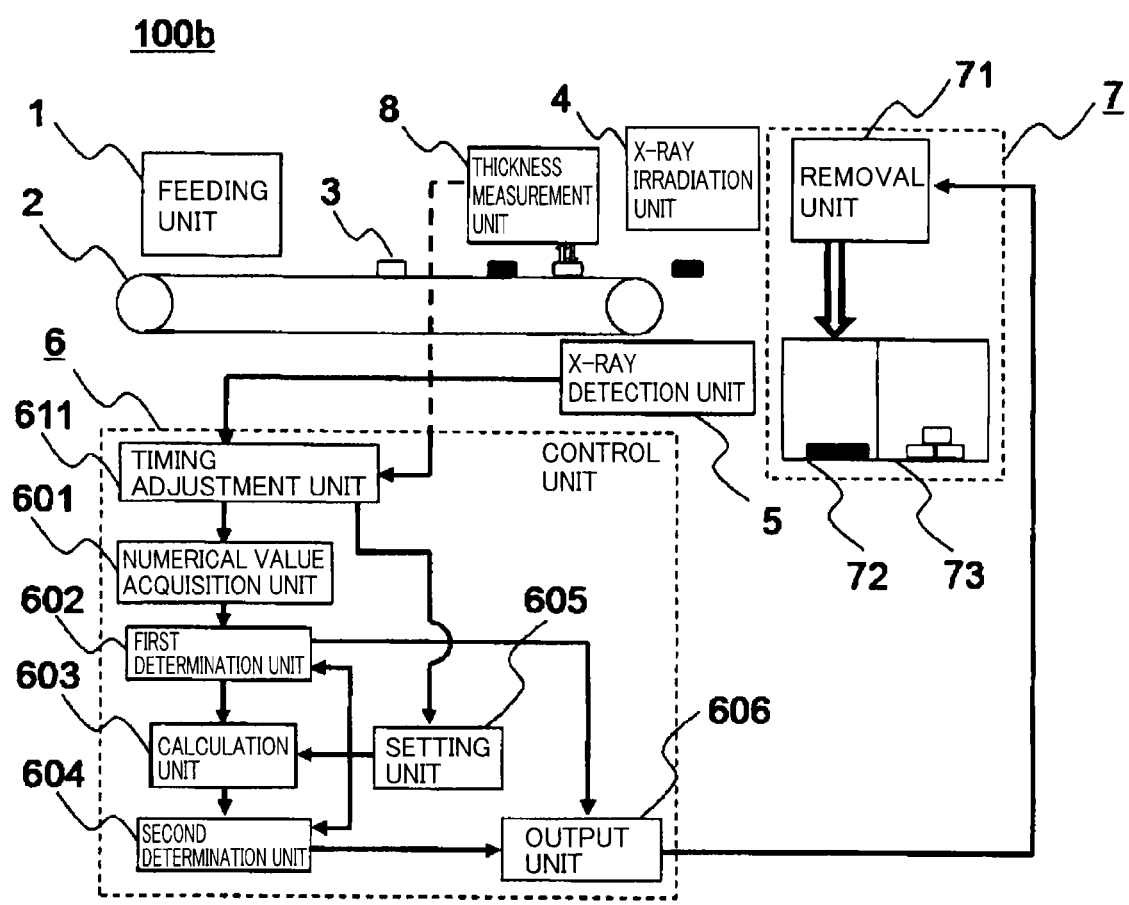
FIG. 16 is a diagram schematically showing a configuration of a sorting apparatus according to a sixth embodiment of the present invention.

FIG. 16 is a diagram schematically showing a configuration of sorting apparatus 100b according to the sixth embodiment of the present invention.

A thickness measurement unit 8 formed of a laser-type thickness gauge or the like and mounted on conveying unit 2 measures the thickness of resin piece 3 conveyed by conveying unit 2. After the thickness is measured, the resin piece is irradiated with an X-ray emitted from X-ray irradiation unit 4, and the intensity of the transmitted X-ray is measured by transmitted X-ray detection unit 5, similarly to the above-described procedure. In order to associate the result of measurement of the thickness and the result of measurement of the intensity of the transmitted X-ray with each other for one resin piece 3, the timing is adjusted by a timing adjustment unit 611.

Timing adjustment unit 611 calculates a delay time to irradiation with the X-ray, according to the rate of feeding by conveying unit 2 to associate the data. Since conveying unit 2 has a uniform width, thickness measurement unit 8 acquires information about the position in the width direction perpendicular to the conveying direction, simultaneously with acquiring the measurement of the thickness, in order to differentiate between resin pieces 3 conveyed in parallel.

Based on the thickness data, control unit 6 selects an appropriate category of the thickness, and uses determination parameters corresponding to the selected category, to successively determine whether resin piece 3 is a useful resin piece or an object to be removed. Based on the result of measurement by thickness measurement unit 8, control unit 6 sets Threshold Value 1, Threshold Value 2, and differential value parameter k to be used for determination. These parameters are set in advance by setting unit 605, in the form of a data table corresponding to the categories of the thickness of resin piece 3. As to the result of measurement of the thickness and the procedure of selecting the parameters, the present embodiment is similar to the third embodiment as described above. The step of sorting resin piece 3 by sorting unit 7 based on the result of the determination is also similar to that of the above-described embodiment.

While resin-piece sorting apparatus 100b has an apparatus configuration where thickness measurement unit 8 is added to resin-piece sorting apparatus 100 shown in FIG. 14, thickness measurement unit 8 may be added to resin-piece sorting apparatus 100a shown in FIG. 15. In this case, differential value parameters k1, k2, k3 corresponding respectively to thickness categories T1, T2, T3 . . . of resin piece 3 for example are calculated. For any configuration, the thickness measurement data can be used to improve the sorting accuracy.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A resin piece sorting method comprising:
an X-ray inspection step of irradiating a resin piece with X-rays including a first X-ray and a second X-ray having respective energy ranges different from each other and measuring a first transmission intensity which is an intensity of the first X-ray transmitted through said resin piece and a second transmission intensity which is an intensity of the second X-ray transmitted through said resin piece;
a first determination step of making a determination as to whether said resin piece is a candidate for a useful resin piece, using said first transmission intensity;
a second determination step of making a determination as to whether a resin piece identified as a candidate for a useful resin piece in said first determination step is a useful resin piece, using a differential value obtained from said first transmission intensity and said second transmission intensity; and
a collection step of collecting a resin piece identified as useful based on a result of the determination in said second determination step.

2. The resin piece sorting method according to claim 1, wherein
said first determination step includes the step of determining, from the fact that said first transmission intensity is equal to or more than a first threshold value, said resin piece is a candidate for a useful resin piece, and
said second determination step includes the step of determining, from the fact that said differential value is equal to or more than a second threshold value, said resin piece is a useful resin piece.

3. The resin piece sorting method according to claim 2, comprising the steps of:
storing said first transmission intensity; and
correcting said first threshold value, using a plurality of said stored first transmission intensities, wherein
said first determination step includes the step of making said determination for a subsequent resin piece, using said corrected first threshold value.

4. The resin piece sorting method according to claim 2, comprising the steps of:

storing said first transmission intensity and said second transmission intensity; and
correcting a differential value parameter for calculating the differential value, using a plurality of said stored first transmission intensities and second transmission intensities, wherein
said second determination step includes the step of making said determination for a subsequent resin piece, using said corrected differential value parameter.

5. The resin piece sorting method according to claim 4, comprising the step of correcting said second threshold value, using a plurality of said stored first transmission intensities, wherein
said second determination step includes the step of making said determination for a subsequent resin piece, using said corrected second threshold value.

6. The resin piece sorting method according to claim 2, comprising the steps of:
measuring the thickness of said resin piece, prior to said X-ray inspection step; and
setting said first threshold value, according to said measured thickness of said resin piece.

7. The resin piece sorting method according to claim 4, comprising the steps of:
measuring the thickness of said resin piece, prior to said X-ray inspection step; and
setting said differential value parameter, according to said measured thickness of said resin piece.

8. The resin piece sorting method according to claim 2, comprising the steps of:
measuring the thickness of said resin piece, prior to said X-ray inspection step; and
setting said second threshold value, according to said measured thickness of said resin piece.

9. A resin piece sorting apparatus comprising:
a conveying unit conveying a resin piece;
an X-ray irradiation unit irradiating said resin piece with X-rays including a first X-ray and a second X-ray having respective energy ranges different from each other;
an intensity-of-transmitted-X-ray measurement unit measuring a first transmission intensity which is an intensity of the first X-ray transmitted through said resin piece and a second transmission intensity which is an intensity of the second X-ray transmitted through said resin piece;
a first determination unit making a determination as to whether said resin piece is a candidate for a useful resin piece, using said first transmission intensity;
a second determination unit making a determination as to whether a resin piece identified as a candidate for a useful resin piece by said first determination unit is a useful resin piece, using a differential value obtained from said first transmission intensity and said second transmission intensity; and
a sorting unit sorting and collecting said resin piece, based on a result of the determination by said second determination unit.

* * * * *

UNITED STATES PATENT AND TRADEMARK OFFICE
CERTIFICATE OF CORRECTION

PATENT NO. : 9,566,615 B2  
APPLICATION NO. : 14/826536  
DATED : February 14, 2017  
INVENTOR(S) : Noriyuki Fujii et al.

Page 1 of 1

It is certified that error appears in the above-identified patent and that said Letters Patent is hereby corrected as shown below:

Column 8, Line 5, correct formula (3) from "$\log_e (I_L / I_0) = \mu_L t$" to -- $\log_e (I_L / I_0) = -\mu_L t$ --.

Column 10, Lines 7 & 8, correct the term "$\mu_L/\mu H > \mu_{0L}/\mu_{0H}$" to -- $\mu_L/\mu_H > \mu_{0L}/\mu_{0H}$ --.

Signed and Sealed this  
Tenth Day of April, 2018

Andrei Iancu  
*Director of the United States Patent and Trademark Office*